US007893021B2

(12) United States Patent
Cantor

(10) Patent No.: US 7,893,021 B2
(45) Date of Patent: Feb. 22, 2011

(54) PARATHYROID HORMONE ANTAGONISTS AND USES THEREOF

(75) Inventor: Thomas L. Cantor, El Cajon, CA (US)

(73) Assignee: Scantibodies Laboratory, Inc., Santee, CA (US)

(*) Notice: Subject to any disclaimer, the term of this patent is extended or adjusted under 35 U.S.C. 154(b) by 1235 days.

(21) Appl. No.: 10/215,770

(22) Filed: Aug. 9, 2002

(65) Prior Publication Data
US 2003/0087822 A1 May 8, 2003

Related U.S. Application Data

(63) Continuation-in-part of application No. 09/323,606, filed on Jun. 1, 1999, now abandoned, and a continuation-in-part of application No. 09/928,047, filed on Aug. 10, 2001, now Pat. No. 6,923,968, and a continuation-in-part of application No. 09/636,530, filed on Aug. 10, 2001, now abandoned.

(60) Provisional application No. 60/224,446, filed on Aug. 10, 2000, provisional application No. 60/224,447, filed on Aug. 10, 2000.

(51) Int. Cl.
A61K 38/29 (2006.01)
(52) U.S. Cl. .......................... 514/2; 530/324
(58) Field of Classification Search ........................ None
See application file for complete search history.

(56) References Cited

U.S. PATENT DOCUMENTS

| 4,086,196 | A | | 4/1978 | Tregear ..................... 260/112.5 |
|---|---|---|---|---|
| 4,423,037 | A | | 12/1983 | Rosenblatt et al. .......... 424/177 |
| 4,508,828 | A | | 4/1985 | Lindall et al. |
| 4,656,250 | A | | 4/1987 | Morita et al. ............... 530/324 |
| 4,968,669 | A | | 11/1990 | Rosenblatt et al. ............ 514/12 |
| 5,093,233 | A | | 3/1992 | Rosenblatt et al. ......... 435/7.21 |
| 5,171,670 | A | * | 12/1992 | Kronenberg et al. ....... 435/68.1 |
| 5,208,041 | A | | 5/1993 | Sindrey ...................... 424/562 |
| 5,229,489 | A | | 7/1993 | Kanmera et al. ............ 530/324 |
| 5,252,705 | A | * | 10/1993 | Kanmera et al. ............ 530/324 |
| 5,317,010 | A | | 5/1994 | Pang et al. .................... 514/12 |
| 5,317,029 | A | * | 5/1994 | Inazu et al. .................. 514/422 |
| 5,382,658 | A | | 1/1995 | Kronis et al. ............... 530/397 |
| 5,434,246 | A | | 7/1995 | Fukuda et al. .............. 530/324 |
| 5,446,130 | A | | 8/1995 | Kanmera et al. ............ 530/324 |
| 5,496,801 | A | | 3/1996 | Holthuis et al. ............... 514/12 |
| 5,563,122 | A | | 10/1996 | Endo et al. .................... 514/12 |
| 5,578,569 | A | * | 11/1996 | Tam ............................. 514/12 |
| 5,589,452 | A | | 12/1996 | Krstenansky et al. ......... 514/12 |
| 5,607,915 | A | | 3/1997 | Patton ........................ 514/12 |
| 5,686,102 | A | | 11/1997 | Gross et al. ................. 424/450 |
| 5,693,616 | A | | 12/1997 | Krstenansky et al. ......... 514/12 |
| 5,695,955 | A | | 12/1997 | Krstenansky et al. ...... 435/69.4 |
| 5,723,577 | A | | 3/1998 | Dong ........................ 530/324 |
| 5,736,154 | A | | 4/1998 | Fuisz ......................... 424/449 |
| 5,741,511 | A | | 4/1998 | Lee et al. .................... 424/449 |
| 5,747,456 | A | | 5/1998 | Chorev et al. ................. 514/12 |
| 5,763,480 | A | * | 6/1998 | Schlesinger et al. ......... 514/476 |
| 5,783,558 | A | | 7/1998 | Duvos et al. .................. 514/12 |
| 5,798,225 | A | | 8/1998 | Krstenansky et al. ...... 435/69.4 |
| 5,807,823 | A | | 9/1998 | Krstenansky et al. ......... 514/12 |
| 5,814,607 | A | | 9/1998 | Patton ........................ 514/12 |
| 5,840,837 | A | | 11/1998 | Krstenansky et al. ....... 530/324 |
| 5,849,695 | A | | 12/1998 | Cohen et al. .................. 514/12 |
| 5,856,138 | A | * | 1/1999 | Fukuda ..................... 435/69.4 |
| 5,869,305 | A | | 2/1999 | Samulski et al. ......... 435/172.3 |
| 5,874,086 | A | | 2/1999 | Krstenansky et al. .... 424/198.1 |
| 5,886,039 | A | | 3/1999 | Kock et al. .................. 514/557 |
| 5,888,767 | A | | 3/1999 | Dropulić et al. ............ 435/69.1 |
| 5,941,868 | A | | 8/1999 | Kaplan et al. ............... 604/500 |
| 5,962,274 | A | | 10/1999 | Parks ........................ 435/91.1 |
| 6,030,790 | A | | 2/2000 | Adermann et al. |
| 6,051,686 | A | | 4/2000 | Krstenansky et al. ....... 530/333 |
| 6,197,801 | B1 | | 3/2001 | Lin ............................ 514/365 |
| 6,258,374 | B1 | | 7/2001 | Friess et al. ................. 424/436 |
| 6,521,597 | B1 | * | 2/2003 | Vickery et al. ................ 514/15 |
| 6,923,968 | B2 | * | 8/2005 | Cantor .................... 424/198.1 |
| 2002/0160945 | A1 | | 10/2002 | Cantor |

FOREIGN PATENT DOCUMENTS

DE 3347548 7/1985

(Continued)

OTHER PUBLICATIONS

Crandell et al. Osteoporosis [online]. Retrieved from the internet <http://www.medicinenet.com/osteoporosis/article.htm>, Dec. 17, 2006.*

(Continued)

Primary Examiner—Anish Gupta
(74) Attorney, Agent, or Firm—Morrison & Foerster LLP

(57) ABSTRACT

The present invention relates to parathyroid hormone (PTH) antagonists. More particularly, the present invention provides for pharmaceutical compositions, kits and combinations comprising the PTH antagonist. The present invention also provides for methods for preventing, treating or delaying a disease or disorder associated with excessive bone mineral, e.g., calcium, loss or for preventing, treating or delaying the effect of a PTH agonist using the PTH antagonist. The present invention further provides for methods for identifying a subject having or at risk of having osteoporosis or decreased bone density, or for identifying a subject in need of PTH antagonist treatment, or for monitoring a subject undergoing treatment for osteoporosis or decreased bone density, by determining and/or monitoring PTH antagonist level or a comparative value between PTH agonist and PTH antagonist. The present invention further provides for methods for identifying an agent suitable for preventing, treating or delaying osteoporosis by identifying a compound that enhances the PTH antagonist activity.

27 Claims, 7 Drawing Sheets

FOREIGN PATENT DOCUMENTS

| | | |
|---|---|---|
| DE | 4434551 | 4/1996 |
| EP | 0451867 | 11/1991 |
| EP | 0783522 | 12/2001 |
| WO | WO-91/06564 | 5/1991 |
| WO | WO 93/06845 | 4/1993 |
| WO | WO-94/03201 | 2/1994 |
| WO | WO-96/10041 | 4/1996 |
| WO | WO 00/42437 | 7/2000 |

OTHER PUBLICATIONS

The Merck Manual. Osteoporosis. Retrieved from the Internet <http://www.merck.com/mmhe/au/print/sec05/ch060/ch060a.html>.*
RxList, The Internet Drug index. Evista Clincal Pharmacology. Retrieved from the Internet <http://www.rxlist.com/cgi/generic/raloxif_cp-page3.htm>.2007 .*
RxList, The Internet Drug Index. . Retrieved from the Internet <http://www.rxlist.com/cgi/generic/alendron_cp-page3.htm>.2007 .*
U.S. Appl. No. 09/231,422, filed Jan. 14, 1999.
U.S. Appl. No. 09/344,639, filed Jun. 26, 1999.
U.S. Appl. No. 09/636,530, filed Aug. 10, 2001.
U.S. Appl. No. 09/636,531, filed Aug. 10, 2000.
U.S. Appl. No. 09/928,047, filed Aug. 10, 2001.
U.S. Appl. No. 09/928,048, filed Aug. 10, 2001.
U.S. Appl. No. 10/002,818, filed Nov. 2, 2001.
U.S. Appl. No. 60/224,396, filed Aug. 10, 2000.
Abilgaard et al. "Long-Term Oral Pamidronate Treatment Inhibits Osteoclastic Bone Resorption and Bone Turnover Without Affecting Osteoblastic Function in Multiple Myeloma" Eur J Haematol 61(2):128-34 (1998) [Abstract] at <http://www.ncbi.nlm.nih.gov> (Visited Oct. 24, 2001).
Abilgaard et al. "Biochemical Markers of Bone Metabolism Reflect Osteoclastic and Osteoblastic Activity in Multiple Myeloma" Eur J. Haematol. 64(2):121-129 (2000) [Abstract] at <http://www.ncbi.nlm.nih.gov> (Visited Oct. 24, 2001).
Apperley and Croucher. "Bisphosphonates in Multiple Myeloma" Pathol Biol. (Paris) 47(2):178-181 (1999) [Abstract] at <http://www.ncbi.nlm.nih.gov> (Visited Oct. 24, 2001).
Baker et al. Anal. Biochem. 239:20-24 (1996).
Bataille et al. "Quantifiable Excess of Bone Resorption in Monoclonal Gammopathy is an Early Symptom of Malignancy: A Prospective Study of 87 Bone Biopsies" Blood 87(11):1462-9 (1996) [Abstract] at <http://www.ncbi.nlm.nih.gov> (Visited Oct. 24, 2001).
Baum et al. Anal. Biochem. 237:129-134 (1996).
Beaudreuil and Orcel. "[Bone Hyperresorption in Multiple Myeloma]" Presse Med 29(9):492-7 (2000) [Abstract] at <http://www.ncbi.nlm.nih.gov> (Visited Oct. 24, 2001).
Berenson and Lipton. "Bisphosphonates in the Treatment of Malignant Bone Disease" Annu Rev Med 50:237-248 (1999) [Abstract] at <http://www.ncbi.nlm.nih.gov> (Visited Oct. 24, 2001).
Berenson. "New Advances in the Biology and Treatment of Myeloma Bone Disease" Semin. Hematol. 38(2 Suppl 3):15-20 (2001) [Abstract] at <http://www.ncbi.nlm.nih.gov> (Visited Oct. 24, 2001).
Bethune et al. Endocrinology 81:67-70 (1967).
Braunwalder et al. J. Biolmol. Screening 1:23-26 (1996).
Brewer et al. Proc. Natl. Acad. Sci. USA 69(12):3585-3588 (1972).
Brewer and Ronan. Proc. Natl. Acad. Sci. USA 67(4):1862-1869 (1970).
Broach et al. "High Throughput Screening for Drug Discovery" Nature 384:14-16 (1996).
Burbaum et al. "New Technologies for High-Throughput Screening" Curr. Opin. Chem. Biol. 1:72-78 (1997).
Caligaris-Cappio et al. "Role of Bone Marrow Stromal Cells in the Growth of Human Multiple Myeloma" Blood 77(12):2688-2693 (1991) [Abstract] at <http://www.ncbi.nlm.nih.gov> (Visited Oct. 24, 2001).
Caligaris-Cappio et al. "In Vitro Growth of Human Multiple Myeloma: Implications for Biology and Therapy" Hematol Oncol Clin North Am 6(2):257-271 (1992) [Abstract] at <http://www.ncbi.nlm.nih.gov> (Visited Oct. 24, 2001).
Causton et al. J. Endocrinology 33:1-12 (1965).
Chen et al. J. Biol. Chem. 271:25308-25315 (1996).
Clezardin. "[Bone Hyperresorption in Bone Metastases]" Presse Med 29(9):487-91 (2000) [Abstract] at <http://www.ncbi.nlm.nih.gov> (Visited Oct. 24, 2001).
Coleman. "Management of Bone Metastases" Oncologist 5(6):463-70 (2000) [Abstract] at <http://www.ncbi.nlm.nih.gov> (Visited Oct. 24, 2001).
Coleman. "Optimising Treatment of Bone Metastases by Aredia and Zometa" 7(4):361-369 (2000) [Abstract] at <http://www.ncbi.nlm.nih.gov> (Visited Oct. 24, 2001).
Coleman. "Should Bisphosphonates be the Treatment of Choice for Metastatic Bone Disease?" Semin Oncol. 28(4 Suppl 11): 35-41 (2001) [Abstract] at <http://www.ncbi.nlm.nih.gov> (Visited Oct. 24, 2001).
Cruz et al. "Ibandonate Decreases Bone Disease Development and Osteoclast Stimulatory Activity in an In Vivo Model of Human Myeloma" Exp. Hematol. 29(4):441-7 (2001) [Abstract] at <http://www.ncbi.nlm.nih.gov> (Visited Oct. 24, 2001).
Dacke and Kenny. Endocrinology 92:463-470 (1973).
Divietti et al. "In Vitro Inhibition of Bone Resorption by Human PTH(7-84)" J. Bone Miner Res. 16(Suppl 1):S307 (2001).
Divietti et al. "Human PTH-(7-84) Inhibits Bone Resorption In Vitro Via Actions Independent of the Type 1 PTH/PTHrP Receptor" Endocrinology 143:171-176 (2002).
Dresner-Pollak et al. "Evaluation In Vivo of a Potent Parathyroid Hormone Antagonist: [Nle8, 18,D-Trp12, Tyr34,]bPTH(7-34)NH2" Journal of Bone and Mineral Research 11(8):1061-1065 (1996).
Durie et al. "Establishment of Two New Myeloma Cell Lines from Bilateral Pleural Effusions: Evidence for Sequential In Vivo Clonal Change" Blood 66(3):548-55 (1985) [Abstract] at <http://www.ncbi.nlm.nih.gov> (Visited Oct. 24, 2001).
Faugere et al. "The Effects of PTH-(1-84) on Bone Turnover Are Antagonized by PTH-(7-84) in Thyroparathyroidectomized and Nephrectomized Rats" J Am Soc Nephrol 12:764A (2001) [Abstract].
Faust et al. "Multiple Myeloma Cells and Cells of the Human Osteoclast Lineage Share Morphological and Cell Surface Markers" J Cell Biochem 71(4):559-68 (1998) [Abstract] at <http://www.ncbi.nlm.nih.gov> (Visited Oct. 24, 2001).
Fernandes. "Letter from the Society President" J. Biomol. Screening 2:1 (1997).
Führ et al. Klin Wochenschr 33:729-730 (1955).
Garrett et al. "A Murine Model of Human Myeloma Bone Disease" 20(6):515-20 (1997) [Abstract] at <http://www.ncbi.nlm.nih:gov> (Visited Oct. 24, 2001).
Gonzalez et al. Biophys. J. 69:1272-1280 (1995).
Harvey and Lipton. "The Role of Bisphosphonates in Treatment of Bone Metastases- The U.S. Experience" Support Care Cancer 4(3):213-7 (1996) [Abstract] at <http://www.ncbi.nlm.nih.gov> (Visited Oct. 24, 2001).
Heinrich et al. J. Biol. Chem. 259(5):3320-3329 (1984).
Hjorth-Hansen et al. "Marked Osteoblastopenia and Reduced Bone Formation in a Model of Multiple Myeloma Bone Disease in Severe Combined Immunodeficiency Mice" J. Bone Miner Res 14(2):256-263 (1999)[Abstract] at <http://www.ncbi.nlm.nih.gov> (Visited Oct. 24, 2001).
Jameson et al. Methods Enzymol. 246:283-300 (1995).
Janzen et al. "High Throughput Screening as a Discovery Tool in the Pharmaceutical Industry" Lab Robotics Automation 8:261-265 (1996).
Jolley. Biomol. Screening 1:33-38 (1996).
Kanis and McCloskey. "Bisphosphonates in Multiple Myeloma" Cancer 88(12 Suppl.):3022-3032 (2000) [Abstract] at <http://www.ncbi.nlm.nih.gov> (Visited Oct. 24, 2001).
Karperien et al. Mech. Dev. 47(1):29-42 (1994).
Kiberstis. "Biomedicine: Malignant Loss of Balance" Science 294-269 (2001).
Kozak. Biol. Chem. 266:19867-19870 (1991).

Kronenberg et al. Proc. Natl. Acad. Sci. USA 76(10):4981-4985 (1979).
LePage et al. Clin. Chem. 44:805-810 (1998).
Lerner et al. J. Biomol. Screening 1:135-143 (1996).
Lewis and Taylor. J. Endocrinology 53(3):xlv-xlvi (1972).
Loveridge et al. Endocrinology 128:1938-1946 (1991).
Lynch et al. Anal. Biochem. 247:77-82 (1997).
McCloskey et al. "The Clinical and Cost Considerations of Bisphosphonates in Preventing Bone Complications in Patients with Metastatic Breast Cancer or Multiple Myeloma" Drugs 61(9):1253-1274 (2001) [Abstract] at <http://www.ncbi.nlm.nih.gov> (Visited Oct. 24, 2001).
Monier-Faugere et al. "Improved Assessment of Bone Turnover by the PTH-(1-84)/Large C-PTH Fragments Ratio in ERSD Patients" Kidney International 60:1460-1468 (2001).
Musto. "The Role of Bisphosphonates for the Treatment of Bone Disease in Multiple Myeloma" Leuk Lymphoma 31(5-6):453-462 (1998) [Abstract] at <http://www.ncbi.nlm.nih.gov> (Visited Oct. 24, 2001).
Nogrady. Medicinal Chemistry A Biochemical Approach Oxford University Press, New York pp. 388-392 (1985).
Parsons et al. J. Endocrinology 53(3):43-45 (1972).
Parsons et al. Endocrinology 92(2):454-462 (1973).
Pausova et al. Genomics 20(1):20-26 (1994).
Pavlakis and Stockler. "Bisphosphates for Breast Cancer" Cochrane Database System Rev. (1):CD003474 (2002) at <http://www.ncbi.nlm.nih.gov> (Visited Jun. 3, 2003).
Podbesek et al. Endocrinology 112:1000-1006 (1983).
Rico et al. "Treatment of Multiple Myeloma with Nasal Spray Calcitonin: A Histomorphometric and Biochemical Study" Bone Miner 8(3):231-7 (1990) [Abstract] at <http://www.ncbi.nlm.nih.gov> (Visited Oct. 24, 2001).
Roodman. "Osteoclast Function in Paget's Disease and Multiple Myeloma" Bone 17(2 Suppl):57S-61S (1995) [Abstract] at <http://www.ncbi.nlm.nih.gov> (Visited Oct. 24, 2001).
Rosol et al. Gene 160(2):241-243 (1995).
Schmelzer et al. Nucleic Acids Res. 15(16):6740 (1987).
Shipman et al. "Anti-Tumour Activity of Bisphosphonates in Human Myeloma Cells" Leuk Lymphoma 32(1-2):129-138 (1998) [Abstract] at <http://www.ncbi.nlm.nih.gov> (Visited Oct. 24, 2001).
Shipman et al. "Bisphosphonates- Mechanisms of Action in Multiple Myeloma" Acta Oncol. 39(7):829-835 (2000) [Abstract] at <http://www.ncbi.nlm.nih.gov> (Visited Oct. 24, 2001).
Silverman et al. Curr. Opin. Chem. Biol. 2(3):397-403 (1998).
Sittampalam et al. Curr. Opin. Chem. Biol. 1(3):384-391 (1997).
Slatopolsky et al. "A Novel Mechanism for Skeletal Resistance in Uremia" Kidney International 58:753-761 (2000).
Smith et al. Biochim. Biophys. Acta. 1307(3):339-347 (1996).
Smith and Rivier (Eds.) "Peptides Chemistry and Biology" Proceedings of the Twelfth American Peptide Symposium, Jun. 16-21, Cambridge MA pp. 37-39 (1991).
Sonatore et al. Anal. Biochem. 240:289-297 (1996).
Sullivan et al. J. Biomol. Screening 2:19-23 (1997).
Sung et al. Biochem. Cell Biol. 64(2):133-138 (1986).
Treacher. J. Endocrinology 35:229-238 (1966).
Vasicek et al. Proc. Natl. Acad. Sci. USA 80(8):2127-2131 (1983).
Watson et al. Molecular Biology of the Gene 4$^{th}$ Ed. Bejacmin/Cummings Pub. Co. p. 224 (1987).
Weaver et al. Mol. Cell. Endocrinol: 28(3):411-424 (1982).
Weaver et al. Gene 28(3):319-329 (1984).
Chorey et al., Biochemistry (1990) 29:1580-1586.
Hoare et al., Journal of Biological Chemistry (2000) 275(35):27274-27283.
International Search Report for PCT/US02/25348, mailed on Jul. 26, 2004, 4 pages.
Jonsson et al., Endocrinology (2001) 142(2):704-709.
Pausova et al., Mammalian Genome (1995) 6:408-414.
Takasu et al., Journal of Bone Mineral Metabolism (1994) 12(Suppl. 1):S131-S134.
Yu et al., Endocrinology (1997) 138(8):3085-3092.

Adermann et al., Innovations and Perspectives in Solid Phase Synthesis, Epton (ed.), Mayflower World Wide, Birmingham (1994) pp. 429-432.
Atkinson et al., Journal of Immunoassay (1982) 3(1):31-51.
Blind et al., Clin. Chem. (1987) 33(8):1376-1381.
Bowie et al., Science (1990) 247:1306-1310.
Brossard et al., Journal of Clinical Endocrinology and Metabolism (1996) 81(11):3923-3929.
Campbell, Monoclonal Antibody and Immunosensor Technology, Laboratory Techniques in Biochemistry and Molecular Biology, van der Vliet (ed.), Elsevier (1991) pp. 1-11, 42-45.
Caporale and Rosenblatt, Paraththyroid Hormone Antagonists Effective in vivo, Advances in Experimental Medicine and Biology, New York (1986) pp. 315-327.
Clinical Chemistry (1999) 45(6)Suppl:A97 b, Abstract Nos. 339-341.
D'Amour et al., Am. J. Physiol. (1986) 251:E680-E687.
Daniel et al., Virology (1994) 202:540-549.
Faugere et al., Kidney International (2001) 60:1460-1468.
Faugere et al. Nephrology, Bone & Mineral Metabolism A3995.
Fischer et al., The Journal of Clinical Investigation (1974) 54:1382-1394.
Gao et al., Clinica Chimica Acta (1996) 245:39-59.
Goodman et al., NEJM (2000) 342(20):1478-1483.
Gordon et al., Parathyroid Hormone Domain for Protein Kinase C Stimulation Located within Amphiphilic Helix, Peptides: Chemistry and Biology, Proceedings of the Twelfth American Peptide Symposium, Jun. 16-21, 1991, Cambridge, MA, Smith and Rivier (eds.), Escom Science Publishers (1992) pp. 37-39.
Hashimoto et al. Journal of Cardiovascular Pharmacology (1981) 3(4):668-676.
Hehrmann et al., Journal of Immunoassay (1980) 1(2):151-174.
John et al., Journal of Clinical Endocrinology and Metabolism (1999) 84(11):4287-4290.
Lepage et al., Clin. Chem. (1998) 44:805-810.
Logue et al., Journal of Immunological Methods (1991) 137:159-166.
Mägerlein et al., Arzneim.-Forsch./Drug Res. (1998) 48(1):197-204.
Mägerlein et al., Arzneim.-Forsch./Drug Res. (1998) 48(II):783-787.
Mallette, Journal of Clinical Endocrinology and Metabolism (1980) 50(1):201-203.
Nakamura et al., Endocrinol. JPN (1981) 28(4):547-549.
Ngo et al., The Protein Folding Problem and Tertiary Structure Prediction, Merz et al., (eds.), Birkhäuser Boston (1994) pp. 492-495.
Niall et al., Proc. Natl. Acad. Sci. USA (1974) 71(2):384-388.
Nussbaum et al., Chemical Abstracts (1982) 96(5):181-192.
Pang et al., Pharmacol. Exp. Ther. (1981) 216(3):567-571.
Podbesek et al., (1983). Endocrinology 112(3):1000-1006.
Qi et al., Am. J. Kidney Dis. (1995) 26-622-631.
Quarles et al., J. Clin. Endocrinol. Metab. (1992) 75:145-150.
Stadler, Homologous Radioimmunoassay for Human Parathyroid Hormone (Residues 1-34) with Biotinylated Peptide as Tracer, Calcium Regulating Hormones, Vitamin D Metabolites, and Cyclic AMP Assays and their Clinical Application, Schmidt-Gayk et al., (eds.), Berlin/Heidelberg, Springer, (1990) pp. 137-150.
Tampe et al., J. Immunoassay (1992) 13(1):1-13.
U.S. Appl. No. 09/323,606, filed Jun. 1, 1999 (Cantor).
Visser et al., Acta Endocrinology (1979) 90:90-102.
Wingender et al., Structure-Function Relationship in Parathyroid Hormone, Advances in Protein Design, International Workshop, Blöcker et al. (eds.), VCH (1988) pp. 167-176.
Zanelli et al., Journal of Immunoassay (1983) 4(2):175-206.
Zemplar package insert, Abbott Reference (1998) 06-9998-R1-Rev. Roche Laboratories.
U.S. Appl. No. 09/928,047, filed Aug. 10, 2001.
Preliminary Amendment for U.S. Appl. No. 09/928,047, filed Apr. 11, 2002.
Restriction Requirement for U.S. Appl. No. 09/928,047, date mailed on Sep. 25, 2003.
Response to Restriction Requirement for U.S. Appl. No. 09/928,047, filed Oct. 7, 2003.
Non-Final Office Action for for U.S. Appl. No. 09/928,047, date mailed on Jan. 14, 2004.

Amendment in Response to Non-Final Office Action for U.S. Appl. No. 09/928,047, filed Apr. 14, 2004.
Amendment for U.S. Appl. No. 09/928,047, filed Apr. 14, 2004.
Final Office Action for U.S. Appl. No. 09/928,047, date mailed on Jul. 13, 2004.
Amendment After Final Action for U.S. Appl. No. 09/928,047, filed Dec. 13, 2004.
Statement of Substance of Interview for U.S. Appl. No. 09/928,047, filed Jan. 13, 2005.
Notice of Allowance for U.S. Appl. No. 09/928,047, date mailed on Mar. 9, 2005.
U.S. Appl. No. 09/323,606, filed Jun. 1, 1999.
Non-Final Office Action for U.S. Appl. No. 09/323,606, date mailed on Oct. 8, 1999.
Amendment for U.S. Appl. No. 09/323,606, filed Jun. 7, 2000.
Non-Final Office Action for U.S. Appl. No. 09/323,606, date mailed on Nov. 28, 2000.
Notice of Abandonment for U.S. Appl. No. 09/323,606, date mailed on Jun. 28, 2001.
Petition for Revival of an Application for Patent Abandoned Unintentionally for U.S. Appl. No. 09/323,606, filed Apr. 15, 2002.
Amendment for U.S. Appl. No. 09/323,606, filed Apr. 15, 2002.
Declaration of Thomas L. Cantor for U.S. Appl. No. 09/323,606, filed Apr. 15, 2002.
Notice to Rescind Abandonment and Non-Final Office Action for U.S. Appl. No. 09/323,606, date mailed on Nov. 4, 2003.
Statement of Substance of Interview for U.S. Appl. No. 09/323,606, filed Nov. 8, 2004.
Non-Final Office Action for U.S. Appl. No. 09/323,606, date mailed on Nov. 4, 2004.
Amendment in Response to Non-Final Office Action for U.S. Appl. No. 09/323,606, filed Feb. 4, 2005.
Non-Final Office Action for U.S. Appl. No. 09/323,606, date mailed on Apr. 29, 2005.
Amendment in Response to Non-Final Office Action for U.S. Appl. No. 09/323,606, filed Oct. 31, 2005.
Notice of Allowance for U.S. Appl. No. 09/323,606, date mailed on Aug. 10, 2006.
Request for Continued Examination for U.S. Appl. No. 09/323,606, filed Oct. 2, 2006.
Non-Final Office Action for U.S. Appl. No. 09/323,606, date mailed on Jan. 8, 2007.
Amendment in Response to Non-Final Office Action for U.S. Appl. No. 09/323,606, filed Apr. 6, 2007.
Non-Final Office Action for U.S. Appl. No. 09/323,606, date mailed on Oct. 12, 2007.
U.S. Appl. No. 10/956,760, filed Oct. 1, 2004.
Restriction Requirement for U.S. Appl. No. 10/956,760, date mailed on Mar. 29, 2007.
Response to Restriction Requirement for U.S. Appl. No. 10/956,760, filed Apr. 23, 2007.
Non-Final Office Action U.S. Appl. No. 10/956,760, date mailed on Jul. 16, 2007.
Amendment in Response to Non-Final Office Action U.S. Appl. No. 10/956,760, filed Oct. 16, 2007.

* cited by examiner

PARATHYROID HORMONE ANTAGONISTS AND USES THEREOF

The present application is a continuation-in-part application of the following U.S. patent applications: 1) Ser. No. 09/323,606, filed Jun. 1, 1999; now abandoned 2) Ser. No. 09/928,047, filed Aug. 10, 2001, now U.S. Pat. No. 6,923,968 which claims priority benefit of U.S. provisional application Ser. No. 60/224,446, filed Aug. 10, 2000; and 3) Ser. No. 09/636,530, filed Aug. 10, 2000, now abandoned which claims priority benefit of U.S. provisional application Ser. No. 60/224,447, filed Aug. 10, 2000. The disclosure of the above-referenced applications is incorporated by reference herein in their entireties.

TECHNICAL FIELD

The present invention relates to parathyroid hormone (PTH) antagonists. More particularly, the present invention provides for pharmaceutical compositions, kits and combinations comprising the PTH antagonist. The present invention also provides for methods for preventing, treating or delaying a disease or disorder associated with excessive bone mineral, e.g., calcium, loss or for preventing, treating or delaying the effect of a PTH agonist using the PTH antagonist. The present invention further provides for methods for identifying a subject having or at risk of having osteoporosis or decreased bone density, or for identifying a subject in need of PTH antagonist treatment, or for monitoring a subject undergoing treatment for osteoporosis or decreased bone density, by determining and/or monitoring PTH antagonist level or a comparative value between PTH agonist and PTH antagonist. The present invention further provides for methods for identifying an agent suitable for preventing, treating or delaying osteoporosis by identifying a compound that enhances the PTH antagonist activity.

BACKGROUND OF THE INVENTION

Calcium plays an indispensable role in cell permeability, the formation of bones and teeth, blood coagulation, transmission of nerve impulse, and normal muscle contraction. The concentration of calcium ions in the blood is, along with calcitriol and calcitonin, regulated mainly by parathyroid hormone (PTH). Extracellular calcium levels are directly affected by PTH through calcium uptake in kidney tubule cells and calcium transport to or from bone. Although calcium intake and excretion may vary, PTH serves through a feedback mechanism to maintain a steady concentration of calcium in cells and surrounding fluids. When serum calcium lowers, the parathyroid glands secrete PTH, affecting the release of stored calcium. When serum calcium increases, stored calcium release is retarded through lowered secretions of PTH.

The complete or whole form of human PTH, (hPTH), is a unique 84 amino acid peptide (SEQ ID NO:1), as is shown in FIG. 1. Researchers have found that this peptide has an anabolic effect on bone that involves a domain for protein kinase C activation (amino acid residues 28 to 34) as well as a domain for adenylate cyclase activation (amino acid residues 1 to 7). However, various catabolic forms of clipped or fragmented PTH peptides also are found in circulation, most likely formed by intraglandular or peripheral metabolism. For example, hPTH can be cleaved between amino acids 34 and 35 to produce a (1-34) PTH N-terminal fragment and a (35-84) PTH C-terminal fragment. Likewise, clipping can occur between either amino acids 36 and 37 or 37 and 38. Recently, a large PTH fragment referred to as "non-(1-84) PTH" has been disclosed which is clipped closer to the N-terminal end of PTH. (See R. LePage et al., *Clin. Chem.,* 44:805-810 (1998)).

The cleaved fragments of PTH vary in both biological activity and metabolic clearance rate from the circulation. For example, the N-terminal human $PTH_{1-34}$ ($hPTH_{1-34}$) fragment has PTH agonist properties, but is rapidly removed from circulation. A daily subcutaneous administration of hPTH to patients with idiopathic osteoporosis has been shown to substantially increase their iliac trebecular bone volume. (See Podbesek et al., *Endocrinology,* 112:1000-1006 (1983)).

PTH plays a role in the course of disease in a patient with chronic renal failure. Renal osteodystrophy (RO) is a complex skeletal disease comprising osteitis fibrosa cystica (caused by excess PTH), osteomalacia resulting in mineralized bone matrix (caused by vitamin D deficiency), extraskeletal calcification/ossification (caused by abnormal calcium and phosphorus metabolism), and adynamic bone disease (contributed to by PTH suppression). Chronic renal failure patients can develop RO. Failing kidneys increase serum phosphorus (hyperphosphoremia) and decrease 1,25-dihydroxyvitamin D (1,2S-D) production by the kidney. The former results in secondary hyperparathyroidism from decreased gastrointestinal calcium absorption and osteitis fibrosa cystica from increased PTH in indirect response to an increase in serum phosphorus. The later causes hypocalcemia and osteomalacia. With the onset of secondary hyperparathyroidism, the parathyroid gland becomes less responsive to its hormonal regulators because of decreased expression of its calcium and vitamin D receptors. Serum calcium drops. RO can lead to digital gangrene, bone pain, bone fractures, and muscle weakness.

To treat secondary hyperparathyroidism, patients are given calcium and vitamin D replacement. Vitamin D analogues, such as calcitriol, stimulate intestinal calcium transport, calcium absorption in bone and calcium tubular reabsorption in kidneys. Such therapy has its dangers. Serum calcium levels must be carefully monitored. Too much dosage can induce hypercalcemia or hypercalciuria. Moreover, very serious consequences occur from calcium and phosphorus mismanagement from direct and indirect PTH suppression therapy. Soft tissue calcification results in a five to fifteen times higher incidence of myocardial infarction among end stage renal dialysis patients as compared to age matched diabetes patients. The secondarily hyperplastic parathyroid glands escape PTH control over calcium, a condition referred to as tertiary hyperparathyroidism.

Another treatment proposed for patients with excess PTH is to administer parathyroid hormone analogues which inhibit the biological activity of PTH. U.S. Pat. Nos. 5,093,233 and 4,968,669 disclose N-terminal PTH analogues ($PTH_{7-34}$ and $PTH_{8-34}$), having substitutions at the 8, 12, 18, and/or 34 amino acid positions. These analogs bind to PTH cell surface receptors but do not stimulate a change in the second messenger concentration, i.e., act as a hormone for calcium ion concentration. PTH activity can also be inhibited by unsubstituted PTH fragments, namely $PTH_{3-34}$ or $PTH_{7-34}$, however, these fragments are so weak in their antagonist properties that they do not have practical or beneficial significance.

Osteoporosis is the most common form of metabolic bone disease and may be considered the symptomatic, fracture stage of bone loss (osteopenia). Although osteoporosis may occur secondary to a number of underlying diseases, 90% of all cases appear to be idiopathic. Postmenopausal women are particularly at risk for idiopathic osteoporosis (postmenopausal or Type I osteoporosis). Another high risk group for idiopathic osteoporosis is the elderly of either sex (senile or Type II osteoporosis). Osteoporosis has also been related to corticosteroid use, immobilization or extended bed rest, alcoholism, diabetes, gonadotoxic chemotherapy, hyperprolactinemia, anorexia nervosa, primary and secondary amenorrhea, and oophorectomy.

In the various forms of osteoporosis, mechanical failure bone fractures frequently occur which are the result of bone loss. Postmenopausal osteoporosis is characterized by fractures of the wrist and spine, while femoral neck fractures seem to be the dominant feature of senile osteoporosis.

Bone loss in osteoporotics is believed to involve an imbalance in the process by which the skeleton renews itself. This process has been termed bone remodeling. It occurs in a series of discrete pockets of activity. These pockets appear spontaneously within the bone matrix on a given bone surface as a site of bone resorption. Osteoclasts (bone dissolving or resorbing cells) are responsible for the resorption of a portion of bone of generally constant dimension. Resorption is followed by the appearance of osteoblasts (bone forming cells) that refill the cavity left by the osteoclasts with new bone.

In a healthy adult subject, the rate at which osteoclasts and osteoblasts are formed is such that bone formation and bone resorption are in balance constituting an optimal bone turnover rate. However, in osteoporotics an imbalance in the bone remodeling process develops which results in bone being lost at a rate faster than it is being made. Although this imbalance occurs to some extent in most individuals as they age, it is much more severe and occurs at a younger age in postmenopausal osteoporotics or following oophorectomy.

There have been many attempts to treat osteoporosis with the goal of either slowing further bone loss or, more desirably, producing a net gain in bone mass. Certain agents, such as estrogen and the bisphosphonates, appear to slow further bone loss in osteoporotics. Agents which slow bone loss, because of the different durations of bone resorption and formation, may appear to increase bone mass (on the order of 3% to 7%). However, this apparent increase is limited in time, not progressive, and is due to a decrease in "remodeling space." In addition, because of the close coupling between resorption and formation, impeding bone resorption also ultimately impedes bone formation.

Another class of agents investigated to combat the onset of osteoporosis encompasses PTH and PTH analogues. (See e.g., U.S. Pat. No. 6,051,686). The theory behind the use of such compounds is to use the body's natural protein receptor binding process to counter a greater removal of calcium from bone than resorption of calcium. Unfortunately, such proposed treatments have had adverse effects, including hypercalcemia (elevated serum calcium) and the formation of osteosarcomas.

There exists a need in the art for more compositions and methods for preventing, treating or delaying a disease or disorder associated with excessive bone mineral, e.g., calcium, loss or for preventing, treating or delaying the effect of a PTH agonist. The present invention addresses this and other related needs in the art.

BRIEF SUMMARY OF THE INVENTION

In one aspect, the present invention is directed to a parathyroid hormone (PTH) antagonist, which PTH antagonist comprises a contiguous portion of human PTH having an amino acid sequence set forth in SEQ ID NO:1 ($PTH_{1-84}$), or a nucleic acid encoding said portion of human PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of $PTH_{1-84}$; and c) said PTH antagonist has a minimal length of three amino acid residues. Preferably, the PTH antagonist is in the form of a pharmaceutical composition, which pharmaceutical composition comprises an effective amount of the PTH antagonist and a pharmaceutically acceptable carrier or excipient. Kits and combinations comprising the PTH antagonist are also provided herein. In a specific embodiment, the PTH antagonist is not $PTH_{7-84}$.

In another aspect, the present invention is directed to a method for preventing, treating or delaying a disease or disorder associated with excessive bone mineral, e.g., calcium, loss in a mammal, which method comprises administering to a mammal, to which such prevention, treatment or delay is needed or desirable, an effective amount of a parathyroid hormone (PTH) antagonist or an agent that enhances production and/or antagonizing function of said PTH antagonist, wherein said PTH antagonist comprises a contiguous portion of human PTH having an amino acid sequence set forth in SEQ ID NO:1 ($PTH_{1-84}$), or a nucleic acid encoding said portion of human PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues, whereby said disease or disorder associated with excessive bone mineral, e.g., calcium, loss is prevented, treated or delayed. In a specific embodiment, the PTH antagonist used in the present method is not $PTH_{7-84}$.

In still another aspect, the present invention is directed to a method for preventing, treating or delaying the effect of a PTH agonist in a mammal, which method comprises administering to a mammal, to which such prevention, treatment or delay is needed or desirable, an effective amount of a parathyroid hormone (PTH) antagonist or an agent that enhances production and/or antagonizing function of said PTH antagonist wherein said PTH antagonist comprises a contiguous portion of human PTH having an amino acid sequence set forth in SEQ ID NO:1 ($PTH_{1-84}$), or a nucleic acid encoding said portion of human PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues, whereby the effect of said PTH agonist is prevented, treated or delayed. In a specific embodiment, the PTH antagonist used in the present method is not $PTH_{7-84}$.

In yet another aspect, the present invention is directed to a method for identifying a subject having or at risk of having osteoporosis or decreased bone density, which method comprises determining PTH antagonist level or a comparative value between PTH agonist and PTH antagonist and identifying a subject having an abnormal PTH antagonist level or an abnormal comparative value between PTH agonist and PTH antagonist as having or at risk of having osteoporosis or decreased bone density. In a specific embodiment, the PTH antagonist used in the present method is not $PTH_{7-84}$.

In yet another aspect, the present invention is directed to a method for identifying a subject in need of parathyroid hormone (PTH) antagonist treatment, which method comprises determining PTH antagonist level or a comparative value between PTH agonist and PTH antagonist and identifying a subject having an abnormal PTH antagonist level or an abnormal comparative value between PTH agonist and PTH antagonist as in need of parathyroid hormone (PTH) antagonist treatment. In a specific embodiment, the PTH antagonist used in the present method is not $PTH_{7-84}$.

In yet another aspect, the present invention is directed to a method for monitoring a subject undergoing treatment for osteoporosis or decreased bone density, which method comprises determining PTH antagonist level or a comparative value between PTH agonist and PTH antagonist and identifying a subject having an abnormal PTH antagonist level or an abnormal comparative value between PTH agonist and PTH antagonist. In a specific embodiment, the PTH antagonist used in the present method is not $PTH_{7-84}$.

In yet another aspect, the present invention is directed to a method for identifying an agent suitable for preventing, treating or delaying osteoporosis, which method comprises: a) measuring PTH antagonist activity in the presence and absence of a test substance (or candidate compound); and b) identifying a test substance (or candidate compound) that enhances said PTH antagonist activity as an agent suitable for preventing, treating or delaying osteoporosis. In a specific embodiment, the PTH antagonist used in the present method is not $PTH_{7-84}$.

In yet another aspect, the present invention is directed to a pharmaceutical composition, which pharmaceutical composition comprises an effective amount of a parathyroid hormone (PTH) antagonist and a pharmaceutically acceptable carrier or excipient, wherein said PTH antagonist comprises a contiguous portion of pig PTH having an amino acid sequence set forth in SEQ ID NO:2 (svseiqlmh nlgkhlssle rvewlrkklq dvhnfvalga sivhrdggsq rprkkednvl veshqkslge adkaavdvli kakpq), dog PTH having an amino acid sequence set forth in SEQ ID NO:3 (svseiqfmh nlgkhlssme rvewlrkklq dvhnfvalga piahrdgssq rplkkednvl vesyqkslge adkadvdvlt kaksq), bovine PTH having an amino acid sequence set forth in SEQ ID NO:4 (avseiqfinh nlgkhlssme rvewlrkklq dvhnfvalga siayrdgssq rprkkednvl veshqkslge adkadvdvli kakpq), rat PTH having an amino acid sequence set forth in SEQ ID NO:5 (avseiqlmh nlgkhlasve rmqwlrkklq dvhnfvslgv qmaaregsyq rptkkeenvl vdgnskslge gdkadvdvlv kaksq), or chicken PTH having an amino acid sequence set forth in SEQ ID NO:6 (svsemqlmh nlgchrhtve rqdwlqmklq dvhsaledar tqrprnkedi vlgeirnnrl lpehlraavq kksidldkay mnvlfktkp), or a nucleic acid encoding said portion of pig, dog, bovine, rat or chicken PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues. In a specific embodiment, the PTH antagonist used in the present pharmaceutical composition is not $PTH_{7-84}$.

In yet another aspect, the present invention is directed to a method for preventing, treating or delaying a disease or disorder associated with excessive bone mineral, e.g., calcium, loss in a mammal, which method comprises administering to a mammal, to which such prevention, treatment or delay is needed or desirable, an effective amount of a parathyroid hormone (PTH) antagonist or an agent that enhances production and/or antagonizing function of said PTH antagonist, wherein said PTH antagonist comprises a contiguous portion of pig PTH having an amino acid sequence set forth in SEQ ID NO:2, dog PTH having an amino acid sequence set forth in SEQ ID NO:3, bovine PTH having an amino acid sequence set forth in SEQ ID NO:4, rat PTH having an amino acid sequence set forth in SEQ ID NO:5 or chicken PTH having an amino acid sequence set forth in SEQ ID NO:6, or a nucleic acid encoding said portion of pig, dog, bovine, rat or chicken PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues, whereby said disease or disorder associated with excessive bone mineral, e.g., calcium, loss is prevented, treated or delayed. In a specific embodiment, the PTH antagonist used in the present method is not $PTH_{7-84}$.

In yet another aspect, the present invention is directed to a method for preventing, treating or delaying the effect of a PTH agonist in a mammal, which method comprises administering to a mammal, to which such prevention, treatment or delay is needed or desirable, an effective amount of a parathyroid hormone (PTH) antagonist or an agent that enhances production and/or antagonizing function of said PTH antagonist, wherein said PTH antagonist comprises a contiguous portion of pig PTH having an amino acid sequence set forth in SEQ ID NO:2, dog PTH having an amino acid sequence set forth in SEQ ID NO:3, bovine PTH having an amino acid sequence set forth in SEQ ID NO:4, rat PTH having an amino acid sequence set forth in SEQ ID NO:5, or chicken PTH having an amino acid sequence set forth in SEQ ID NO:6, or a nucleic acid encoding said portion of pig, dog, bovine, rat or chicken PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues, whereby the effect of said PTH agonist is prevented, treated or delayed. In a specific embodiment, the PTH antagonist used in the present method is not $PTH_{7-84}$.

In yet another aspect, the present invention is directed to a method for preventing, treating or delaying bone metastasis in a human, which method comprises administering to a human, to which such prevention, treatment or delay is needed or desirable, an effective amount of a parathyroid hormone (PTH) antagonist or an agent that enhances production and/or antagonizing function of said PTH antagonist, wherein said PTH antagonist comprises a contiguous portion of human PTH having an amino acid sequence set forth in SEQ ID NO:1 ($PTH_{1-84}$), or a nucleic acid encoding said portion of human PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues, whereby said bone metastasis is prevented, treated or delayed. In a specific embodiment, the PTH antagonist used in the present method is not $PTH_{7-84}$.

BRIEF DESCRIPTION OF THE SEVERAL VIEWS OF THE DRAWING(S)

Figure 3:
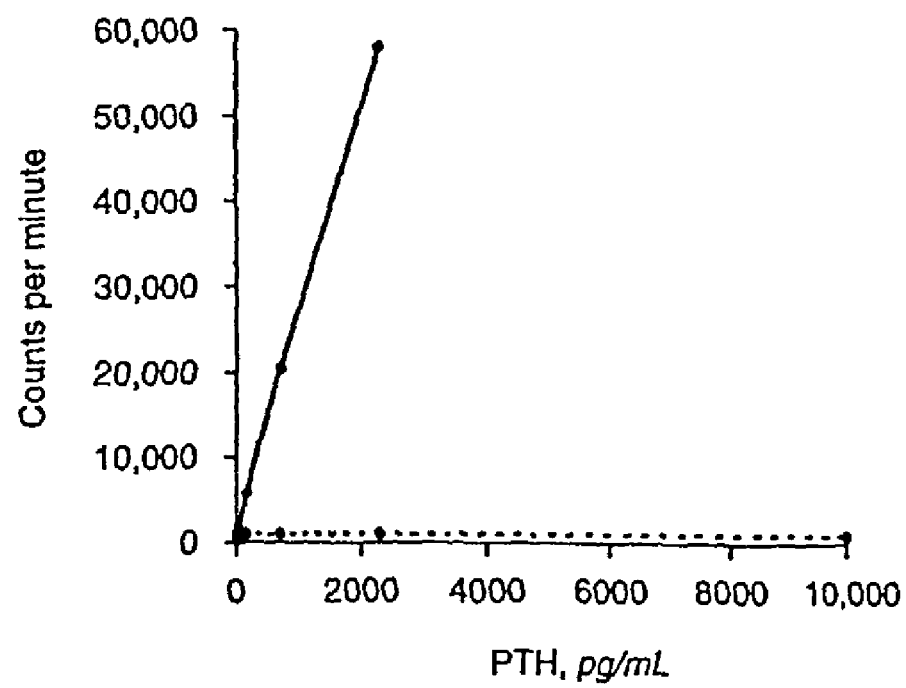

FIG. 3 illustrates comparison of the recognition of hPTH 1-84 and hPTH 7-84 by the Whole PTH assay. Unlike the Nichols I-PTH assay, the Whole PTH assay does discriminate between hPTH 1-84 (solid line) and hPTH 7-84 (dashed line). Concentrations of hPTH 7-84 as high as 10,000 pg were undetectable.

Figure 4:
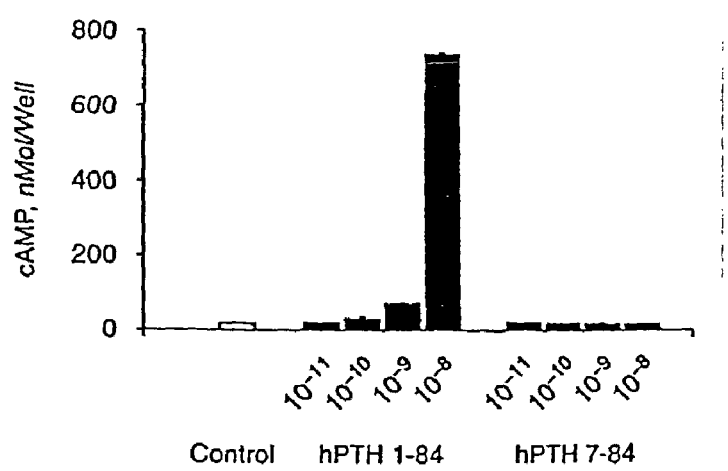

FIG. 4 illustrates comparison of the effect of hPTH 1-84 or hPTH 784 on cAMP production in ROS 17.2 cells. Unlike hPTH 7-84, hPTH 1-84 increased cAMP production in a dose-dependent manner. cAMP increased from $18.1 \pm 1.2$ to $738 \pm 4.1$ nmol/well after treatment with $10^{-8}$ mol/L hPTH 1-84. The same concentration of HPTH 7-84 had no effect.

Figure 5:
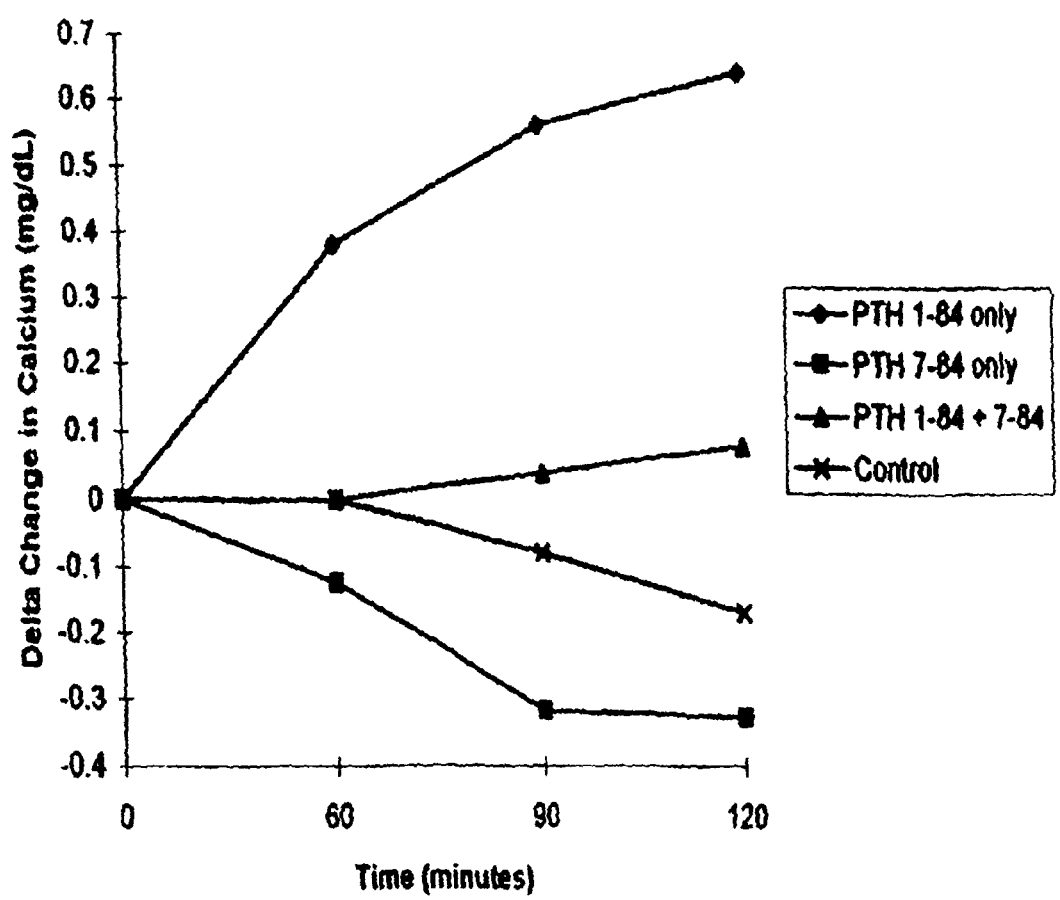

FIG. 5 illustrates comparison of the calcemic effects of PTH isoforms. Parathyroidectomized (PTX) rats fed a 0.02% calcium diet show a significant increase in plasma calcium after treatment with hPTH 1-84. In contrast, hPTH 7-84 produced a slight but significant decrease in plasma calcium. When both peptides were given together in a 1:1 molar ratio, the calcemic response induced by hPTH 1-84 was reduced by 94% ($P<0.001$). Symbols are: (●) 1-84, N=9; (■) 1-84+7-84, N=6; (▲) Control, N=5; (♦)7-84, N=5.

Figure 6:
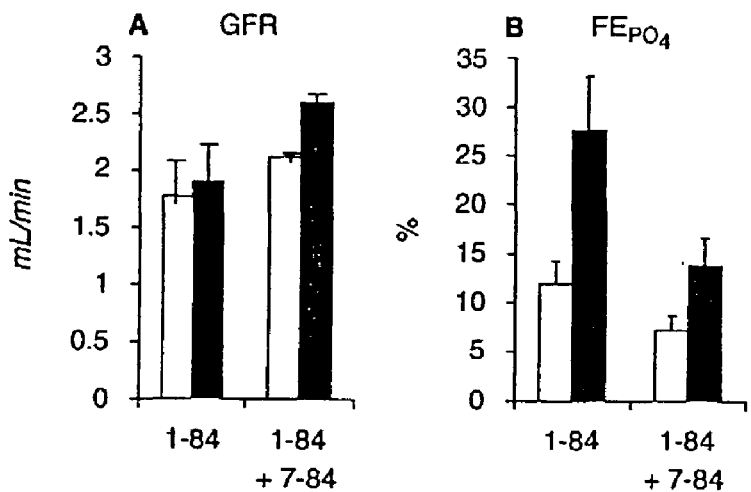

FIG. 6 illustrates comparison of the effects of HPTH 1-84 or hPTH 1-84 plus hPTH 7-84 on (A) glomerular filtration rate (GFR) and (B) fractional excretion of phosphorus ($FE_{po4}$). Control and treatment periods are denoted by open and closed bars, respectively. The phosphaturia induced by HPTH 1-84 was decreased by 50.2% ($P<0.05$) when animals were treated simultaneously with 7-84 PTH, despite a significant increase in GFR ($P<0.005$).

Figure 7:
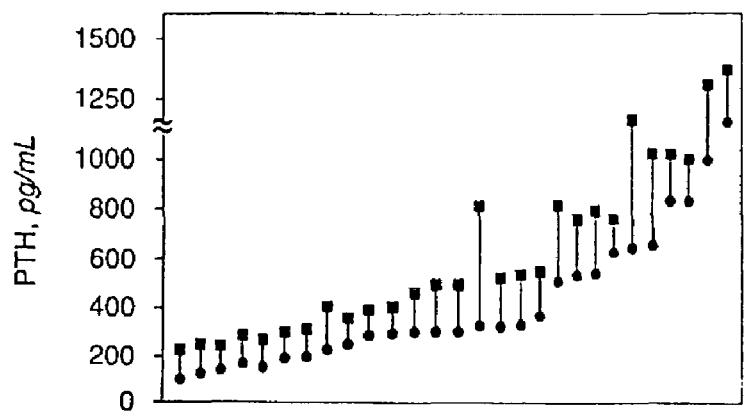

FIG. 7 illustrates comparison of PTH values in plasma from uremic patients using the Nichols "intact" PTH assay (■) versus the Whole PTH assay (●). Plasma PTH values are uniformly higher when measured with the Nichols "intact" PTH assay than with the Whole PTH assay. The median PTH values were 523 vs. 344 pg/mL, respectively ($P<0.001$).

Figure 8:
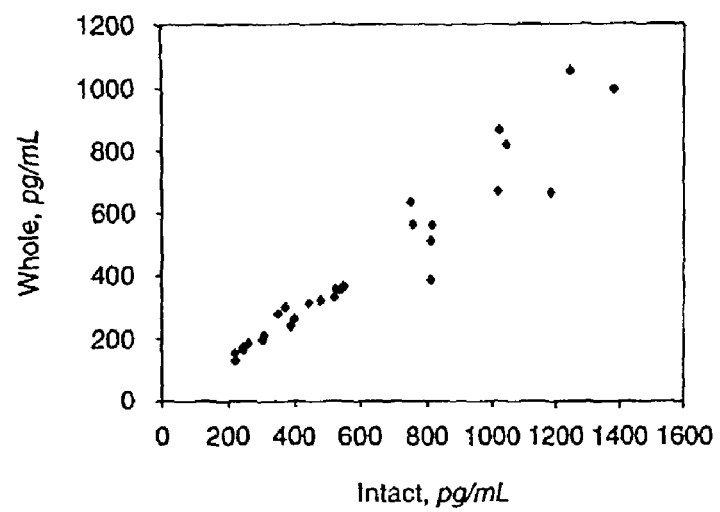

FIG. 8 illustrates regression analysis of plasma PTH measured by Nichols I-PTH and Whole PTH assay in uremic patients ($r=0.97$; $P<0.001$).

Figure 9:
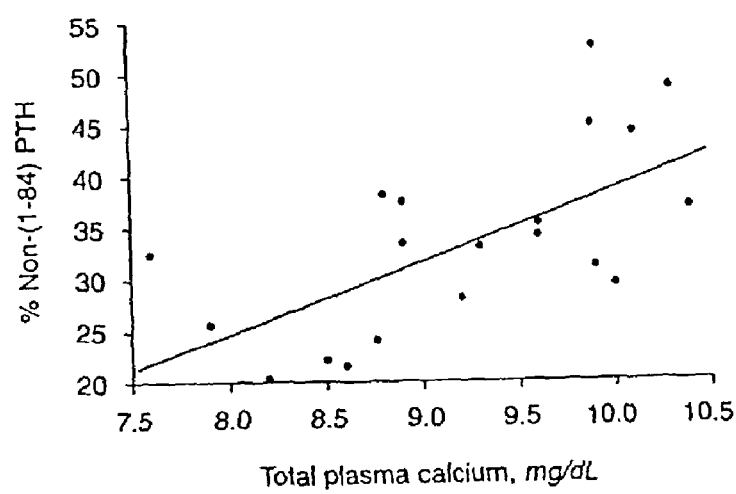

FIG. 9 illustrates effects of plasma calcium on PTH degradation in dialysis patients. The percentage of non-(1-84) PTH fragment (likely hPTH 7-84) correlates positively with plasma calcium ($P<0.02$) ($r=0.638$; $P=0.0025$; N=20).

Figure 10:
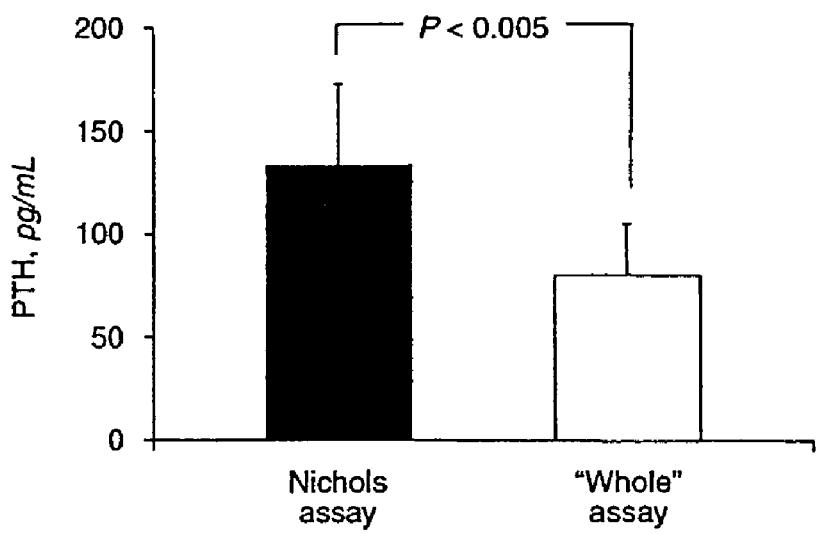

FIG. 10 illustrates comparison of plasma PTH levels in renal transplant patients using Nichols I-PTH and Whole PTH assays. PTH values are higher when measured with the Nichols I-PTH assay ($P>0.005$).

Figure 11:
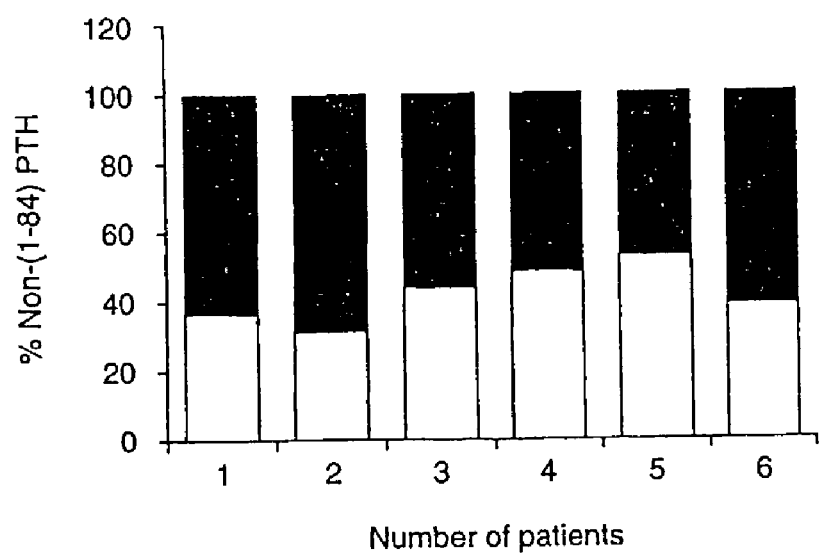

FIG. 11 illustrates intracellular PTH content on parathyroid glands from uremic patients. The $41.8 \pm 3.2\%$ of the total PTH, measured by the I-Nichols assay (expressed as 100%), represents the non-(1-84) PTH fragment "likely" HPTH 7-84 (□). the 1-84 PTH molecule was measured with the Whole PTH assay (■).

DETAILED DESCRIPTION OF THE INVENTION

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "parathyroid hormone (PTH) agonist" refers to the complete molecule of PTH or a fragment or derivative thereof that stimulates osteoclasts formation and bone turnover to increase blood calcium levels. Other names of PTH include parathormone and parathyrin. For purposes herein, the name "parathyroid hormone (PTH)" is used herein, although all other names are contemplated. It is intended to encompass PTH agonist with conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Bejacmin/Cummings Pub. co., p. 224).

As used herein, "parathyroid hormone (PTH) antagonist" refers to a PTH fragment or derivative that counters the effect of a PTH agonist. It is intended to encompass PTH antagonist with conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Bejacmin/Cummings Pub. co., p. 224).

As used herein, a "functional derivative or fragment" of PTH agonist or PTH antagonist refers to a derivative or fragment of PTH that still substantially retains its function as a PTH agonist or PTH antagonist. Normally, the derivative or fragment retains at least 50% of its PTH agonist or PTH antagonist activity. Preferably, the derivative or fragment retains at least 60%, 70%, 80%, 90%, 95%, 99% and 100% of its PTH agonist or PTH antagonist activity. It is also possible that a functional derivative or fragment of PTH agonist or PTH antagonist has higher PTH agonist or PTH antagonist activity than a parent molecule from which the functional derivative or fragment is derived from.

As used herein, "an agent that enhances production of said PTH antagonist" refers to a substance that increases transcription and/or translation of a PTH antagonist, or a substance that increases post-translational modification and/or cellular trafficking of a PTH antagonist precursor, or a substance, e.g., a protease, that cleaves or a substance that enhances the cleavage a PTH protein to generate a PTH antagonist, or a substance that prolongs half-life of a PTH antagonist.

As used herein, an "agent that enhances antagonizing function of said PTH antagonist" refers to a substance that increases potency of the PTH antagonist, or a substance that increases sensitivity of PTH antagonist's natural ligand in a PTH antagonist signaling pathway, or a substance that decreases potency of a PTH agonist.

As used herein, "an abnormal PTH agonist level" refers to: 1) a PTH agonist level in a individual mammal, e.g., human, that is statistically higher or lower than a PTH agonist level in the same individual mammal in a healthy state; 2) a PTH agonist level in a individual mammal, e.g., human, that is statistically higher or lower than a PTH agonist level in another comparable individual mammal in a healthy state; or 3) a PTH agonist level in a individual mammal, e.g., human, that is statistically higher or lower than a mean or average PTH agonist level of comparable healthy population. The difference between the abnormal PTH agonist level and the normal PTH agonist level must be statistically significant so that the difference or the abnormal PTH agonist level can be used in prognosis, diagnosis or treatment monitoring.

As used herein, "an abnormal PTH antagonist level" refers to: 1) a PTH antagonist level in a individual mammal, e.g., human, that is statistically higher or lower than a PTH antagonist level in the same individual mammal in a healthy state; 2) a PTH antagonist level in a individual mammal, e.g., human, that is statistically higher or lower than a PTH antagonist level in another comparable individual mammal in a healthy state; or 3) a PTH antagonist level in a individual mammal, e.g., human, that is statistically higher or lower than a mean or average PTH antagonist level of comparable healthy population. The difference between the abnormal PTH antagonist level and the normal PTH antagonist level must be statistically significant so that the difference or the abnormal PTH antagonist level can be used in prognosis, diagnosis or treatment monitoring.

As used herein, "an abnormal comparative value between PTH agonist and PTH antagonist" refers to: 1) a comparative value between PTH agonist and PTH antagonist in a individual mammal, e.g., human, that is statistically higher or lower than such a comparative value in the same individual mammal in a healthy state; 2) a comparative value between PTH agonist and PTH antagonist in a individual mammal, e.g., human, that is statistically higher or lower than such a comparative value in another comparable individual mammal in a healthy state; or 3) a comparative value between PTH agonist and PTH antagonist in a individual mammal, e.g., human, that is statistically higher or lower than a mean or average comparative value of comparable healthy population. The difference between the abnormal comparative value and the normal comparative value must be statistically significant so that the difference or the abnormal comparative value between PTH agonist and PTH antagonist can be used in prognosis, diagnosis or treatment monitoring. The comparative value between PTH agonist and PTH antagonist can take any suitable form. For example, the comparative value can be a ratio, e.g., PTH agonist/PTH antagonist, PTH antagonist/PTH agonist, PTH agonist/the sum of PTH agonist and PTH antagonist, or PTH antagonist/the sum of PTH agonist and PTH antagonist, etc. In another example, the comparative value can be a subtraction value, e.g., PTH agonist-PTH antagonist, PTH antagonist-PTH agonist, etc. The above examples are for illustration only and are not intended to be an exhaustive list of all possible formats for measuring the comparative value between PTH agonist and PTH antagonist. Other suitable formats are readily apparent to skilled artisans and can be used.

As used herein, "a disease or disorder associated with excessive bone mineral, e.g., calcium, loss" refers to any disease or disorder associated with or caused by net bone loss.

As used herein, "an agent suitable for preventing, treating or delaying a disease or disorder associated with excessive bone mineral, e.g., calcium, loss" does not encompass a PTH antagonist.

As used herein, "an effective amount of a compound for treating a particular disease" is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

As used herein, "treatment" means any manner in which the symptoms of a condition, disorder or disease are ameliorated or otherwise beneficially altered. Treatment also encompasses any pharmaceutical use of the compositions herein.

As used herein, "amelioration" of the symptoms of a particular disorder by administration of a particular pharmaceutical composition refers to any lessening, whether permanent or temporary, lasting or transient that can be attributed to or associated with administration of the composition.

As used herein, "production by recombinant means" refers to production methods that use recombinant nucleic acid methods that rely on well known methods of molecular biology for expressing proteins encoded by cloned nucleic acids.

As used herein, "complementary" when referring to two nucleic acid molecules, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: "stringency of hybridization" in determining percentage mismatch is as follows:
1) high stringency: 0.1×SSPE, 0.1% SDS, 65° C.;
2) medium stringency: 0.2×SSPE, 0.1% SDS, 50° C. (also referred to as moderate stringency); and
3) low stringency: 1.0×SSPE, 0.1% SDS, 50° C.

It is understood that equivalent stringencies may be achieved using alternative buffers, salts and temperatures.

As used herein, "vector (or plasmid)" refers to discrete elements that are used to introduce heterologous DNA into cells for either expression or replication thereof. Selection and use of such vehicles are well known within the skill of the artisan. An expression vector includes vectors capable of expressing DNA's that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eucaryotic cells and/or prokaryotic cells and those that remain episomal or those which integrate into the host cell genome.

As used herein, "a promoter region or promoter element" refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in prokaryotes include the bacteriophage T7 and T3 promoters, and the like.

As used herein, "operatively linked or operationally associated" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, e.g., Kozak, *J. Biol. Chem.*, 266: 19867-19870 (1991)) can be inserted immediately 5' of the start codon and may enhance expression. The desirability of (or need for) such modification may be empirically determined.

As used herein, "pharmaceutically acceptable salts, esters or other derivatives" include any salts, esters or derivatives that may be readily prepared by those of skill in this art using known methods for such derivatization and that produce compounds that may be administered to animals or humans without substantial toxic effects and that either are pharmaceutically active or are prodrugs.

As used herein, a "prodrug" is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

As used herein, "test substance (or candidate compound)" refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, etc.) whose effect on PTH antagonist is determined by the disclosed and/or claimed methods herein.

As used herein, high-throughput screening (HTS) refers to processes that test a large number of samples, such as samples of diverse chemical structures against disease targets to identify "hits" (see, e.g., Broach, et al., High throughput screening for drug discovery, *Nature*, 384:14-16 (1996); Janzen, et al., High throughput screening as a discovery tool in the pharmaceutical industry, *Lab Robotics Automation:* 8261-265 (1996); Fernandes, P. B., Letter from the society president, *J. Biomol. Screening*, 2:1 (1997); Burbaum, et al., New technologies for high-throughput screening, *Curr. Opin. Chem. Biol.*, 1:72-78 (1997)). HTS operations are highly automated and computerized to handle sample preparation, assay procedures and the subsequent processing of large volumes of data.

As used herein, "disease or disorder" refers to a pathological condition in an organism resulting from, e.g., infection or genetic defect, and characterized by identifiable symptoms.

B. Pth Antagonists and Pharmaceutical Composition, Kits and Combinations Comprising the Same In one aspect, the present invention is directed to a parathyroid hormone (PTH) antagonist, which PTH antagonist comprises a contiguous portion of human PTH having an amino acid sequence set forth in SEQ ID NO:1 (PTH$_{1-84}$), or a nucleic acid encoding said portion of human PTH, and said PTH antagonist has the following characteristics: a) the N-terminal amino acid residue of said PTH antagonist starts at any position spanning position 2 through position 33 of said PTH$_{1-84}$; b) the C-terminal amino acid residue of said PTH antagonist ends at any position spanning position 35 through position 84 of said PTH$_{1-84}$; and c) said PTH antagonist has a minimal length of three amino acid residues. Preferably, the PTH antagonist is in the form of a pharmaceutical composition, which pharmaceutical composition comprises an effective amount of the PTH antagonist and a pharmaceutically acceptable carrier or excipient.

The N-terminal amino acid residue of the PTH antagonist can start at any position spanning position 2 through position 33 of said PTH$_{1-84}$. For example, the N-terminal amino acid residue of the PTH antagonist can start at position 2 of the PTH$_{1-84}$. The C-terminal amino acid residue of said PTH antagonist can end at any position spanning position 35 through position 84 of said PTH$_{1-84}$. For example, the C-terminal amino acid residue of the PTH antagonist can end at position 84 of the PTH$_{1-84}$.

In a specific embodiment, the PTH antagonist is a protein or a peptide, or a nucleic acid encoding said protein or peptide, selected from the group consisting of PTH$_{2-84}$, PTH$_{3-84}$, PTH$_{4-84}$, PTH$_{5-84}$, PTH$_{6-84}$, PTH$_{7-84}$, PTH$_{8-84}$, PTH$_{9-84}$, PTH$_{10-84}$, PTH$_{11-84}$, PTH$_{12-84}$, PTH$_{13-84}$, PTH$_{14-84}$, PTH$_{15-84}$, PTH$_{16-84}$, PTH$_{17-84}$, PTH$_{18-84}$, PTH$_{19-84}$, PTH$_{20-84}$, PTH$_{21-84}$, PTH$_{22-84}$, PTH$_{23-84}$, PTH$_{24-84}$, PTH$_{25-84}$, PTH$_{26-84}$, PTH$_{27-84}$, PTH$_{28-84}$, PTH$_{29-84}$, PTH$_{30-84}$, PTH$_{31-84}$, PTH$_{32-84}$, and PTH$_{33-84}$. In another specific embodiment, the PTH antagonist is a protein or a peptide, or a nucleic acid encoding said protein or peptide, selected from the group consisting of PTH$_{7-69}$, PTH$_{7-70}$, PTH$_{7-71}$, PTH$_{772}$, PTH$_{7-73}$, PTH$_{774}$, PTH$_{775}$, PTH$_{7-76}$, PTH$_{7-77}$, PTH$_{7-78}$, PTH$_{7-79}$, PTH$_{7-80}$, PTH$_{7-81}$, PTH$_{7-82}$, PTH$_{7-83}$ and PTH$_{7-84}$.

The PTH antagonist can have any suitable length provided that it maintains its antagonizing activity. For example, the PTH antagonist can have a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82 or 83 amino acid residues.

The PTH antagonist can further comprise an amino acid residue substitution or modification that enhances or does not decrease its antagonist activity, or an amino acid residue substitution or modification that stabilizes the PTH antagonist. For example, the PTH antagonist can further comprise the following amino acid residue substitution or modification: $His_{25}$, $His_{26}$, $Leu_{27}$, (U.S. Pat. No. 5,382,658); $Tyr_{34}$, $D-Trp_{12}$, $Nle_{8,18}$, desamino($Nle_{8,18}$), $Lys_{13}$ modified in the epsilonamino acid group by N,N-diisobutyl or 3-phenylpropanoyl (U.S. Pat. No. 5,093,233); $Gly_{12}$ substituted by D-Trp, L-Trp, L- or D- α- or β-naphthylalanine, or D- or L- α-MeTrp (U.S. Pat. No. 4,968,669); the amino acid residue at positions 7, 11, 23, 24, 27, 28, or 31 being cyclohexylalanine, the amino acid residue at position 3, 16, 17, 18, 19, or 34 being α-aminoisobutyric acid, the amino acid residue at position 1 being α, β-diaminopropionic acid, the amino acid residue at position 27 being homoarginine, the amino acid residue at position 31 being norleucine (U.S. Pat. No. 5,723,577); each of $Arg_{25}$, $Lys_{26}$, $Lys_{27}$ being substituted with Ala, Asn, Asp, Cys, Gln, Glu, Gly, His, Ile, Leu, Met, Phe, Pro, Ser, Thr, Trp, Tyr or Val (U.S. Pat. No. 5,317,010); and a combination thereof.

The PTH antagonist or a pharmaceutical composition comprising the same can be formulated in any suitable formats. For example, the PTH antagonist or a pharmaceutical composition comprising the same can be formulated in a solid or a liquid dosage form. In another example, the PTH antagonist or a pharmaceutical composition comprising the same can be formulated for oral, parenteral, intranasal, topical, or injectable administration, e.g., intracavernous injection, subcutaneous injection, intravenous injection, intramuscular injection and intradermal injection.

If a nucleic acid encoding a PTH antagonist is used, the nucleic acid can be in any suitable forms, e.g., DNA, RNA, PNA or a combination thereof. In a specific example, the nucleic acid can be comprised in a gene therapy vector, e.g., an adenovirus associated vector, a retroviral vector, an adenovirus vector, and a lentivirus vector.

PTH antagonist proteins or functional derivatives or fragments thereof, or a nucleic acid encoding PTH antagonist, or functional derivatives or fragments thereof, can be prepared by any methods known in the art, e.g., synthetic methods, recombinant methods or a combination thereof (See generally, Ausubel (Ed.) *Current Protocols in Molecular Biology*, John Wiley & Sons, Inc. (2000)).

PTH antagonist proteins or functional derivatives or fragments thereof, or a nucleic acid encoding PTH antagonist, or functional derivatives or fragments thereof, derived from know PTH encoding gene can also be used, e.g. AF251060 (Homo sapiens parathyroid hormone); AF130257 (Macaca fascicularis parathyroid hormone); AH007117 (Mus musculus parathyroid hormone); AF066075 (Mus musculus parathyroid hormone); U15662 (Canis familiaris parathyroid hormone, Rosol et al., *Gene*, 160(2):241-243 (1995)); M26143 (Synthetic human parathyroid hormone, Sung et al., *Biochem. Cell Biol.*, 64(2):133-138 (1986)); L19475 (rat parathyroid hormone, Pausova et al., *Genomics*, 20(1):20-26 (1994)); U17418 (human parathyroid hormone); K01938 (Bovine parathyroid hormone, Weaver et al., *Gene*, 28(3): 319-329 (1984)); M25082 (Bovine parathyroid hormone, Weaver et al., *Mol. Cell. Endocrinol.*, 28(3):411-424 (1982)); P41593 (mouse parathyroid hormone, Karperien et al., *Mech. Dev.*, 47(1):29-42 (1994)); (rat parathyroid hormone, Heinrich et al., *J. Biol. Chem.*, 259(5):3320-3329 (1984)); P50133 (porcine parathyroid hormone, Smith et al., *Biochim. Biophys. Acta*, 1307(3):339-347 (1996)); P01270 (human preproparathyroid hormone, Vasicek et al., *Proc. Natl. Acad. Sci. U.S.A.*, 80(8):2127-2131 (1983)); P01268 (bovine preproparathyroid hormone, Kronenberg et al., *Proc. Natl. Acad. Sci. U.S.A.*, 76(10):4981-4985 (1979)); PTHU (parathyroid hormone precursor—human, Brewer et al., *Proc. Natl. Acad. Sci. U.S.A.*, 69(12):3585-3588 (1972)); PTBO (parathyroid hormone precursor—bovine, Brewer and Ronan, *Proc. Natl. Acad. Sci. U.S.A.*, 67(4:1862-1869 (1970); P01269 (preproparathyroid hormone from pig and rat, Schmelzer et al., *Nucleic Acids Res.*, 15(16):6740 (1987)).

In another aspect, the present invention is directed to a kit, which kit comprises a PTH antagonist or a pharmaceutical composition comprising the same in a container and an instruction for using the pharmaceutical composition in preventing, treating or delaying a disease or disorder associated with excessive bone mineral, e.g., calcium, loss or for balancing the effect of excess PTH agonist. For example, the kit can be used in preventing, treating or delaying hyperparathyroidism, renal osteodystrophy, osteoporosis, parathyroid cancer, hypercalcemia, an immune disease and hypertension (See U.S. Pat. No. 4,423,037).

In still another aspect, the present invention is directed to a combination, which combination comprises an effective amount of a parathyroid hormone (PTH) antagonist and an effective amount of an agent suitable for preventing, treating or delaying a disease or disorder associated with excessive bone mineral, e.g., calcium, loss, wherein said PTH antagonist comprises a contiguous portion of human PTH having an amino acid sequence set forth in SEQ ID NO:1 ($PTH_{1-84}$), or a nucleic acid encoding said portion of human PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues.

Any suitable PTH antagonist, including the ones described above, can be used in the present combination. Any suitable agent suitable for preventing, treating or delaying a disease or disorder associated with excessive bone mineral, e.g., calcium, loss can be used in the present combination. For example, in treating osteoporosis, the PTH antagonist can be used in combination with known therapeutics such as calcium, bisphosphanate or vitamin D treatment. Preferably, the present combination further comprises a pharmaceutically acceptable carrier or excipient.

In yet another aspect, the present invention is directed to a parathyroid hormone (PTH) antagonist, which PTH antagonist comprises a contiguous portion of pig PTH having an amino acid sequence set forth in SEQ ID NO:2, dog PTH having an amino acid sequence set forth in SEQ ID NO:3, bovine PTH having an amino acid sequence set forth in SEQ ID NO:4, rat PTH having an amino acid sequence set forth in SEQ ID NO:5, or chicken PTH having an amino acid sequence set forth in SEQ ID NO:6, or a nucleic acid encoding said portion of pig, dog, bovine, rat or chicken PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues. Preferably, the PTH antagonist is in the form of a pharmaceutical composition, which pharmaceutical composition comprises an effective amount of the PTH antagonist and a pharmaceutically acceptable carrier or excipient.

C. Methods Using Pth Antagonist

Methods for Preventing, Treating or Delaying Excessive Bone Mineral, e.g., Calcium, Loss In one aspect, the present invention is directed to a method for preventing, treating or delaying a disease or disorder associated with excessive bone mineral, e.g., calcium, loss in a mammal, which method comprises administering to a mammal, to which such prevention, treatment or delay is needed or desirable, an effective amount of a parathyroid hormone (PTH) antagonist or an agent that enhances production and/or antagonizing function of said PTH antagonist, wherein said PTH antagonist comprises a contiguous portion of human PTH having an amino acid sequence set forth in SEQ ID NO:1 ($PTH_{1-84}$), or a nucleic acid encoding said portion of human PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues, whereby said disease or disorder associated with excessive bone mineral, e.g., calcium, loss is prevented, treated or delayed.

The present method can be used for preventing, treating or delaying a disease or disorder associated with excessive bone mineral, e.g., calcium, loss in any mammals, such as mice, rats, rabbits, cats, dogs, pigs, cows, ox, sheep, goats, horses, monkeys and other non-human primates. Preferably, the present method can be used for preventing, treating or delaying a disease or disorder associated with excessive bone mineral, e.g., calcium, loss in humans. For example, the human to be treated: a) is in need of increased bone density or bone healing; b) has undergone or is presently undergoing corticosteroid therapy, chemotherapy for post menopausal bone loss, radiation therapy for cancer or hormone replacement therapy; c) is immobilized or subjected to extended bed rest due to bone injury; d) suffers from alcoholism, diabetes, hyperprolactinemia, anorexia nervosa, primary and secondary amenorrhea, or oophorectomy; e) is 50 years or older; f) is a female, especially a female who is 40 years or older or is in the post-menopausal stage; or g) is a male.

In a specific embodiment, the human to be treated has an abnormal PTH antagonist level or an abnormal comparative value between PTH agonist and PTH antagonist. The abnormal comparative value between PTH agonist and PTH antagonist can be determined by any suitable formats, e.g., as a ratio, a proportion or a subtraction value. In one example, the abnormal comparative value between PTH agonist and PTH antagonist is determined by determining and comparing at least two of the parameters selected from the group consisting of the level of the PTH agonist, the PTH antagonist and the total PTH level, i.e., a sum of PTH agonist and PTH antagonist. In another example, the human to be treated has a PTH agonist/PTH antagonist ratio more than 2 and the method is used to bring the PTH agonist/PTH antagonist ratio within a range from about 1 to about 2.

The present method can be used in preventing, treating or delaying any disease or disorder associated with excessive bone mineral, e.g., calcium, loss in a mammal. Exemplary diseases or disorders associated with excessive bone mineral loss, e.g., calcium loss, include hyperparathyroidism, renal osteodystrophy, osteoporosis and parathyroid cancer.

Any suitable PTH antagonists can be used in the present methods. The N-terminal amino acid residue of the PTH antagonist can start at any position spanning position 2 through position 33 of said $PTH_{1-84}$. For example, the N-terminal amino acid residue of the PTH antagonist can start at position 2 of the $PTH_{1-84}$. The C-terminal amino acid residue of said PTH antagonist can end at any position spanning position 35 through position 84 of said $PTH_{1-84}$. For example, the C-terminal amino acid residue of the PTH antagonist can end at position 84 of the $PTH_{1-84}$.

In a specific embodiment, the PTH antagonist is a protein or a peptide, or a nucleic acid encoding said protein or peptide, selected from the group consisting of $PTH_{2-84}$, $PTH_{3-84}$, $PTH_{4-84}$, $PTH_{5-84}$, $PTH_{6-84}$, $PTH_{7-84}$, $PTH_{8-84}$, $PTH_{9-84}$, $PTH_{10-84}$, $PTH_{11-84}$, $PTH_{12-84}$, $PTH_{13-84}$, $PTH_{14-84}$, $PTH_{15-84}$, $PTH_{16-84}$, $PTH_{17-84}$, $PTH_{18-84}$, $PTH_{19-84}$, $PTH_{20-84}$, $PTH_{21-84}$, $PTH_{22-84}$, $PTH_{23-84}$, $PTH_{24-84}$, $PTH_{25-84}$, $PTH_{26-84}$, $PTH_{27-84}$, $PTH_{28-84}$, $PTH_{29-84}$, $PTH_{30-84}$, $PTH_{31-84}$, $PTH_{32-84}$, and $PTH_{33-84}$. In another specific embodiment, the PTH antagonist is a protein or a peptide, or a nucleic acid encoding said protein or peptide, selected from the group consisting of $PTH_{7-69}$, $PTH_{7-70}$, $PTH_{7-71}$, $PTH_{7-72}$, $PTH_{7-73}$, $PTH_{7-74}$, $PTH_{7-75}$, $PTH_{7-76}$, $PTH_{7-77}$, $PTH_{7-78}$, $PTH_{7-79}$, $PTH_{7-80}$, $PTH_{7-81}$, $PTH_{7-82}$, $PTH_{7-83}$ and $PTH_{7-84}$.

The PTH antagonist can have any suitable length provided that it maintains its antagonizing activity. For example, the PTH antagonist can have a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82 or 83 amino acid residues.

The PTH antagonist can further comprise an amino acid residue substitution or modification that enhances or does not decrease its antagonist activity, or an amino acid residue substitution or modification that stabilizes the PTH antagonist. For example, the PTH antagonist can further comprise the following amino acid residue substitution or modification: $His_{25}$, $His_{26}$, $Leu_{27}$, (U.S. Pat. No. 5,382,658); $Tyr_{34}$, $D\text{-}Trp_{12}$, $Nle_{8,18}$, desamino($Nle_{8,18}$), $Lys_{13}$ modified in the epsilonamino acid group by N,N-diisobutyl or 3-phenylpropanoyl (U.S. Pat. No. 5,093,233); $Gly_{12}$ substituted by D-Trp, L-Trp, L- or D- α- or β-naphthylalanine, or D- or L- α-MeTrp (U.S. Pat. No. 4,968,669); the amino acid residue at positions 7, 11, 23, 24, 27, 28, or 31 being cyclohexylalanine, the amino acid residue at position 3, 16, 17, 18, 19, or 34 being α-aminoisobutyric acid, the amino acid residue at position 1 being α,β-diaminopropionic acid, the amino acid residue at position 27 being homoarginine, the amino acid residue at position 31 being norleucine (U.S. Pat. No. 5,723,577); each of $Arg_{25}$, $Lys_{26}$, $Lys_{27}$ being substituted with Ala, Asn, Asp, Cys, Gln, Glu, Gly, His, Ile, Leu, Met, Phe, Pro, Ser, Thr, Trp, Tyr or Val (U.S. Pat. No. 5,317,010); and a combination thereof.

The PTH antagonist or a pharmaceutical composition comprising the same can be formulated in any suitable formats. For example, the PTH antagonist or a pharmaceutical composition comprising the same can be formulated in a solid or a liquid dosage form. In another example, the PTH antagonist or a pharmaceutical composition comprising the same can be formulated for oral, parenteral, intranasal, topical, or injectable administration, e.g., intracavernous injection, subcutaneous injection, intravenous injection, intramuscular injection and intradermal injection.

If a nucleic acid encoding a PTH antagonist is used, the nucleic acid can be in any suitable forms, e.g., DNA, RNA, PNA or a combination thereof. In a specific example, the nucleic acid can be comprised in a gene therapy vector, e.g., an adenovirus associated vector, a retroviral vector, an adenovirus vector, and a lentivirus vector.

The PTH antagonist can be administered in any suitable regimen. In one example, the PTH antagonist is administered as a bolus. In another example, the PTH antagonist is administered continuously. In still another example, the PTH antagonist is administered intermittently or is multiply administered. In yet another example, the PTH antagonist is administered over a course of about 1, 2, 2-6, 6-12, or 12-24 hours. In yet another example, the PTH antagonist is administered over a course of about 1, 2, 2-5, 5-14, or 14-60 days. In yet another example, the PTH antagonist is administered over a course of about 1, 2, 2-6, 6-12, 12-24, 24-48, or more months. In yet another example, the PTH antagonist is administered intraperitoneally daily for about 2 months and then the administration is stopped for about 1 month and then resumed intraperitoneally daily for about 2 months.

In one specific embodiment, the human to be treated has undergone or is presently undergoing PTH agonist therapy, and the method is used to prevent, treat or delay excessive bone mineral, e.g., calcium, loss caused by or associated with the PTH agonist therapy. Preferably, the method is used to prevent, treat or delay bone density decrease caused by or associated with said PTH agonist therapy. The PTH agonist used in the PTH agonist therapy can be any suitable PTH agonist, e.g., the one having the PTH adenylate cyclase activating activity. Also preferably, the human to be treated has an abnormal PTH agonist and/or PTH antagonist level.

In another aspect, the present invention is directed to a method for preventing, treating or delaying a disease or disorder associated with excessive bone mineral, e.g., calcium, loss in a mammal, which method comprises administering to a mammal, to which such prevention, treatment or delay is needed or desirable, an effective amount of a parathyroid hormone (PTH) antagonist or an agent that enhances production and/or antagonizing function of said PTH antagonist, wherein said PTH antagonist comprises a contiguous portion of pig PTH having an amino acid sequence set forth in SEQ ID NO:2, dog PTH having an amino acid sequence set forth in SEQ ID NO:3, bovine PTH having an amino acid sequence set forth in SEQ ID NO:4, rat PTH having an amino acid sequence set forth in SEQ ID NO:5, or chicken PTH having an amino acid sequence set forth in SEQ ID NO:6, or a nucleic acid encoding said portion of pig, dog, bovine, rat or chicken PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues, whereby said disease or disorder associated with excessive bone mineral, e.g., calcium, loss is prevented, treated or delayed.

Methods for Preventing, Treating or Delaying the Effect of a PTH Agonist

In another aspect, the present invention is directed to a method for preventing, treating or delaying the effect of a PTH agonist in a mammal, which method comprises administering to a mammal, to which such prevention, treatment or delay is needed or desirable, an effective amount of a parathyroid hormone (PTH) antagonist or an agent that enhances production and/or antagonizing function of said PTH antagonist wherein said PTH antagonist comprises a contiguous portion of human PTH having an amino acid sequence set forth in SEQ ID NO:1 ($PTH_{1-84}$), or a nucleic acid encoding said portion of human PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues, whereby the effect of said PTH agonist is prevented, treated or delayed.

The present method can be used for preventing, treating or delaying the effect of any PTH agonist, e.g., the effect of a PTH agonist that has the PTH adenylate cyclase activating activity or for preventing, treating or delaying the effect of a human PTH agonist. Preferably, the PTH agonist to be countered by the present method comprises a contiguous portion of human PTH having an amino acid sequence set forth in SEQ ID NO:1 ($PTH_{1-84}$), or a nucleic acid encoding said portion of human PTH, and said PTH agonist has the following characteristics: a) the N-terminal amino acid residue of said PTH agonist starts at position 1 of said $PTH_{1-84}$; and b) the C-terminal amino acid residue of said PTH agonist ends at any position spanning position 34 through position 84 of said $PTH_{1-84}$.

In a specific embodiment, the human to be treated has an abnormal PTH antagonist level or an abnormal comparative value between PTH agonist and PTH antagonist. The abnormal comparative value between PTH agonist and PTH antagonist can be determined by any suitable formats, e.g., as a ratio, a proportion or a subtraction value. In one example, the abnormal comparative value between PTH agonist and PTH antagonist is determined by determining and comparing at least two of the parameters selected from the group consisting of the level of the PTH agonist, the PTH antagonist and the total PTH level, i.e., a sum of PTH agonist and PTH antagonist. In another example, the human to be treated has a PTH agonist/PTH antagonist ratio more than 2 and the method is used to bring the PTH agonist/PTH antagonist ratio within a range from about 1 to about 2.

The present method can be used for preventing, treating or delaying a disease or disorder associated with excessive PTH agonist effect. For example, the present method can be used for treating hypercalcemia, hyperparathyroidism, pseudohypoparathyroidism, a hypercalcemic crisis resulted from hyperparathyroidism, hyperparathyroidism caused by renal failure, a tumor producing a parathyroid hormone-like substance, an immune disease such as inflammation, an allergic response or hyperactive lymphocytes, or hypertension.

In one specific embodiment, the human to be treated is undergoing a calcium or vitamin D treatment, e.g., for treating osteoporosis, and the method further comprises a step of monitoring the PTH antagonist level or a comparative value between PTH agonist and PTH antagonist to guide the administration of calcium or vitamin D in the patient.

In still another aspect, the present invention is directed to a method for preventing, treating or delaying the effect of a PTH agonist in a mammal, which method comprises administering to a mammal, to which such prevention, treatment or delay is needed or desirable, an effective amount of a parathyroid hormone (PTH) antagonist or an agent that enhances production and/or antagonizing function of said PTH antagonist, wherein said PTH antagonist comprises a contiguous portion of pig PTH having an amino acid sequence set forth in SEQ ID NO:2, dog PTH having an amino acid sequence set forth in SEQ ID NO:3, bovine PTH having an amino acid sequence set forth in SEQ ID NO:4, rat PTH having an amino acid sequence set forth in SEQ ID NO:5 or chicken PTH having an amino acid sequence set forth in SEQ ID NO:6, or a nucleic acid encoding said portion of pig, dog, bovine, rat or chicken PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues, whereby the effect of said PTH agonist is prevented, treated or delayed.

Methods for Identifying Risk of Having Osteoporosis or Decreased Bone Density

In yet another aspect, the present invention is directed to a method for identifying a subject having or at risk of having osteoporosis or decreased bone density, which method comprises determining PTH antagonist level or a comparative value between PTH agonist and PTH antagonist and identifying a subject having an abnormal PTH antagonist level or an abnormal comparative value between PTH agonist and PTH antagonist as having or at risk of having osteoporosis or decreased bone density.

In a specific embodiment, the human to be treated has an abnormal PTH antagonist level or an abnormal comparative value between PTH agonist and PTH antagonist. The abnormal comparative value between PTH agonist and PTH antagonist can be determined by any suitable formats, e.g., as a ratio, a proportion or a subtraction value. In one example, the abnormal comparative value between PTH agonist and PTH antagonist is determined by determining and comparing at least two of the parameters selected from the group consisting of the level of the PTH agonist, the PTH antagonist and the total PTH level, i.e., a sum of PTH agonist and PTH antagonist. In another example, the human to be treated has a PTH agonist/PTH antagonist ratio more than 2 and the method is used to bring the PTH agonist/PTH antagonist ratio within a range from about 1 to about 2.

Methods for Identifying a Subject in Need of PTH Antagonist Treatment

In yet another aspect, the present invention is directed to a method for identifying a subject in need of parathyroid hormone (PTH) antagonist treatment, which method comprises determining PTH antagonist level or a comparative value between PTH agonist and PTH antagonist and identifying a subject having an abnormal PTH antagonist level or an abnormal comparative value between PTH agonist and PTH antagonist as in need of parathyroid hormone (PTH) antagonist treatment.

In a specific embodiment, the human to be treated has an abnormal PTH antagonist level or an abnormal comparative value between PTH agonist and PTH antagonist. The abnormal comparative value between PTH agonist and PTH antagonist can be determined by any suitable formats, e.g., as a ratio, a proportion or a subtraction value. In one example, the abnormal comparative value between PTH agonist and PTH antagonist is determined by determining and comparing at least two of the parameters selected from the group consisting of the level of the PTH agonist, the PTH antagonist and the total PTH level, i.e., a sum of PTH agonist and PTH antagonist. In another example, the human to be treated has a PTH agonist/PTH antagonist ratio more than 2 and the method is used to bring the PTH agonist/PTH antagonist ratio within a range from about 1 to about 2, by using a PTH antagonist or an agent that enhances production and/or antagonizing function of said PTH antagonist to the identified subject.

Any suitable PTH antagonist, including the ones disclosed above, can be used in the present method. Preferably, the PTH antagonist comprises a contiguous portion of human PTH having an amino acid sequence set forth in SEQ ID NO:1 ($PTH_{1-84}$), or a nucleic acid encoding said portion of human PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues.

D. The Formulation, Dosage and Route of Administration of Pth Antagonist

The formulation, dosage and route of administration of PTH antagonist protein, or a functional fragment thereof, or a nucleic acid encoding an PTH antagonist protein, or a functional fragment thereof, or an agent that enhances production and/or antagonizing function of said PTH antagonist, preferably in the form of pharmaceutical compositions, can be determined according to the methods known in the art (see e.g., *Remington: The Science and Practice of Pharmacy*, Alfonso R. Gennaro (Editor) Mack Publishing Company, April 1997; *Therapeutic Peptides and Proteins: Formulation, Processing, and Delivery Systems*, Banga, 1999; and *Pharmaceutical Formulation Development of Peptides and Proteins*, Hovgaard and Frkjr (Ed.), Taylor & Francis, Inc., 2000; *Medical Applications of Liposomes*, Lasic and Papahadjopoulos (Ed.), Elsevier Science, 1998; *Textbook of Gene Therapy*, Jain, Hogrefe & Huber Publishers, 1998; *Adenoviruses: Basic Biology to Gene Therapy*, Vol. 15, Seth, Landes Bioscience, 1999; *Biopharmaceutical Drug Design and Development*, Wu-Pong and Rojanasakul (Ed.), Humana Press, 1999; *Therapeutic Angiogenesis: From Basic Science to the Clinic*, Vol. 28, Dole et al. (Ed.), Springer-Verlag New York, 1999). The PTH antagonist protein, or a functional fragment thereof, or a nucleic acid encoding an PTH antagonist protein, or a functional fragment thereof, or an agent that enhances production and/or antagonizing function of said PTH antagonist, can be formulated for oral, rectal, topical, inhalational, buccal (e.g., sublingual), parenteral (e.g., subcutaneous, intramuscular, intradermal, or intravenous), transdermal administration or any other suitable route of administration. The most suitable route in any given case will depend on the nature and severity of the condition being treated and on the nature of the particular PTH antagonist protein, or a functional fragment thereof, or a nucleic acid encoding an PTH antagonist protein, or a functional fragment thereof, which is being used.

The PTH antagonist protein, or a functional fragment thereof, or a nucleic acid encoding an PTH antagonist protein, or a functional fragment thereof, or an agent that enhances production and/or antagonizing function of said PTH antagonist, can be administered alone. Alternatively and preferably, the PTH antagonist protein, or a functional fragment thereof, or a nucleic acid encoding an PTH antagonist protein, or a functional fragment thereof, or an agent that enhances production and/or antagonizing function of said PTH antagonist, is co-administered with a pharmaceutically acceptable carrier or excipient. Any suitable pharmaceutically acceptable carrier or excipient can be used in the present method (See e.g., *Remington: The Science and Practice of Pharmacy*, Alfonso R. Gennaro (Editor) Mack Publishing Company, April 1997).

The present method can be used alone. Alternatively, the present method can be used in combination with other agent suitable for preventing, treating or delaying a disease or disorder associated with excessive bone mineral, e.g., calcium, loss. Such other agent can be used before, with or after the administration of PTH antagonist protein, or a functional fragment thereof, or a nucleic acid encoding an PTH antagonist protein, or a functional fragment thereof, or an agent that enhances production and/or antagonizing function of said PTH antagonist. For example, the PTH antagonist protein, or a functional fragment thereof, or a nucleic acid encoding an PTH antagonist protein, or a functional fragment thereof, or an agent that enhances production and/or antagonizing function of said PTH antagonist, can be co-administered with such other agent.

The nucleic acid encoding an PTH antagonist protein, or a functional fragment thereof, can be used in the form of naked DNA, complexed DNA, cDNA, plasmid DNA, RNA or other mixtures thereof as components of the gene delivery system. In another embodiment, the nucleic acid encoding a PTH antagonist protein, or a functional fragment thereof, is included in a viral vector. Any viral vectors that are suitable for gene therapy can used in the combination. For example, an adenovirus vector (U.S. Pat. No. 5,869,305), a simian virus vector (U.S. Pat. No. 5,962,274), a conditionally replicating human immunodeficiency viral vector (U.S. Pat. No. 5,888,767), retrovirus, SV40, Herpes simplex viral amplicon vectors and Vaccinia virus vectors can be used. In addition, the genes can be delivered in a non-viral vector system such as a liposome wherein the lipid protects the DNA or other biomaterials from oxidation during the coagulation.

According to the present invention, the PTH antagonist protein, or a functional fragment thereof, or a nucleic acid encoding an PTH antagonist protein, or a functional fragment thereof, or an agent that enhances production and/or antagonizing function of said PTH antagonist, alone or in combination with other agents, carriers or excipients, may be formulated for any suitable administration route, such as intracavernous injection, subcutaneous injection, intravenous injection, intramuscular injection, intradermal injection, oral or topical administration. The method may employ formulations for injectable administration in unit dosage form, in ampoules or in multidose containers, with an added preservative. The formulations may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, sterile pyrogen-free water or other solvents, before use. Topical administration in the present invention may employ the use of a foam, gel, cream, ointment, transdermal patch, or paste.

Pharmaceutically acceptable compositions and methods for their administration that may be employed for use in this invention include, but are not limited to those described in U.S. Pat. Nos. 5,736,154; 6,197,801 B1; 5,741,511; 5,886,039; 5,941,868; 6,258,374 B1; and 5,686,102.

The magnitude of a therapeutic dose in the treatment or prevention will vary with the severity of the condition to be treated and the route of administration. The dose, and perhaps dose frequency, will also vary according to age, body weight, condition and response of the individual patient.

It should be noted that the attending physician would know how to and when to terminate, interrupt or adjust therapy to lower dosage due to toxicity, or adverse effects. Conversely, the physician would also know how to and when to adjust treatment to higher levels if the clinical response is not adequate (precluding toxic side effects).

Any suitable route of administration may be used. Dosage forms include tablets, troches, cachet, dispersions, suspensions, solutions, capsules, patches, and the like. See, Remington's Pharmaceutical Sciences.

In practical use, the PTH antagonist protein, or a functional fragment thereof, or a nucleic acid encoding an PTH antagonist protein, or a functional fragment thereof, or an agent that enhances production and/or antagonizing function of said PTH antagonist, alone or in combination with other agents, may be combined as the active in intimate admixture with a pharmaceutical carrier or excipient, such as beta-cyclodextrin and 2-hydroxy-propyl-beta-cyclodextrin, according to conventional pharmaceutical compounding techniques. The carrier may take a wide form of preparation desired for administration, topical or parenteral. In preparing compositions for parenteral dosage form, such as intravenous injection or infusion, similar pharmaceutical media may be employed, water, glycols, oils, buffers, sugar, preservatives, liposomes, and the like known to those of skill in the art. Examples of such parenteral compositions include, but are not limited to dextrose 5% w/v, normal saline or other solutions. The total dose of the PTH antagonist protein, or a functional fragment thereof, or a nucleic acid encoding an PTH antagonist protein, or a functional fragment thereof, or an agent that enhances production and/or antagonizing function of said PTH antagonist, alone or in combination with other agents to be administered may be administered in a vial of intravenous fluid, ranging from about 1 ml to 2000 ml. The volume of dilution fluid will vary according to the total dose administered.

The invention also provides for kits for carrying out the therapeutic regimens of the invention. Such kits comprise in one or more containers therapeutically effective amounts of the PTH antagonist protein, or a functional fragment thereof, or a nucleic acid encoding an PTH antagonist protein, or a functional fragment thereof, or an agent that enhances production and/or antagonizing function of said PTH antagonist, alone or in combination with other agents, in pharmaceutically acceptable form. Preferred pharmaceutical forms would be in combination with sterile saline, dextrose solution, or buffered solution, or other pharmaceutically acceptable sterile fluid. Alternatively, the composition may be lyophilized or dessicated; in this instance, the kit optionally further comprises in a container a pharmaceutically acceptable solution, preferably sterile, to reconstitute the complex to form a solution for injection purposes. Exemplary pharmaceutically acceptable solutions are saline and dextrose solution.

In another embodiment, a kit of the invention further comprises a needle or syringe, preferably packaged in sterile form, for injecting the composition, and/or a packaged alcohol pad. Instructions are optionally included for administration of composition by a physician or by the patient.

In specific embodiments, formulations disclosed in the following U.S. Patent Nos. can be used. U.S. Pat. No. 5,496,801 discloses a PTH formulation using mannitol as excipient and citrate as buffering agent, and are incorporated in vials as a freeze-dried powder for reconstitution to treat osteoporosis. U.S. Pat. No. 5,607,915 discloses systemic delivery of parathyroid hormone to a mammalian host by inhalation through the mouth of a dispersion of an N-terminal fragment of PTH. It has been found that such respiratory delivery of the PTH fragment provides a pulsatile concentration profile of the PTH in the host's serum. PTH fragment compositions include dry powder formulations having the PTH present in a dry bulking powder, liquid solutions or suspensions suitable for nebulization, and aerosol propellants suitable for use in a metered dose inhaler. U.S. Pat. No. 5,563,122 discloses a safe, stabilized lyophilized preparation comprising PTH as an active ingredient and effective amounts of sugar and sodium chloride to provide a stable preparation of parathyroid hormone. The sugar can be a monosaccharide, e.g., mannitol, glucose, sorbitol, inositol, and or a disaccharide, e.g., sucrose, maltose, lactose or trehalose.

E. Methods for Monitoring Treatment for Osteoporosis or Decreased Bone Density In yet another aspect, the present invention is directed to a method for monitoring a subject undergoing treatment for osteoporosis or decreased bone density, which method comprises determining PTH antagonist level or a comparative value between PTH agonist and PTH antagonist and identifying a subject having an abnormal PTH antagonist level or an abnormal comparative value between PTH agonist and PTH antagonist.

The abnormal comparative value between PTH agonist and PTH antagonist can be determined by any suitable formats, e.g., as a ratio, a proportion or a subtraction value. In one example, the abnormal comparative value between PTH agonist and PTH antagonist is determined by determining and comparing at least two of the parameters selected from the group consisting of the level of the PTH agonist, the PTH antagonist and the total PTH level, i.e., a sum of PTH agonist and PTH antagonist. In another example, the human to be treated has a PTH agonist/PTH antagonist ratio more than 2. In still another example, the subject, e.g., a human, has PTH agonist-PTH antagonist value that equals or is more than 50 pg/ml. In yet another example, the subject, e.g., a human, has a PTH agonist level that is more than PTH antagonist level. The present method can further comprise a step to bring the PTH agonist/PTH antagonist ratio within a range from about 1 to about 2, by using a PTH antagonist or an agent that enhances production and/or antagonizing function of said PTH antagonist to the identified subject.

In a specific embodiment, the subject, e.g., a human, is undergoing a calcium, bisphosphanate or vitamin D treatment. This way, the present method can be used to guide the calcium, bisphosphanate or vitamin D treatment in order for those agents to be useful in stimulating the correct amount of PTH antagonist as an osteoclast inhibitor for the treatment of osteoporosis and high bone turnover. The new discovery here is that calcium and vitamin D cause a preferential stimulation of PTH antagonist which acts directly on the bone to lower bone turnover by inhibiting the osteoclasts (Divietti et al., *Endocrinology*, 143:171-176 (2002); and Divietti et al., *J. Bone Miner. Res.*, 16:Suppl 1, S307 (2001)). Accordingly, the present method can be used to monitor the effectiveness of the calcium, bisphosphanate or vitamin D treatment for osteoporosis and high bone turnover by measuring both the absolute increase in PTH antagonist and the increase in PTH antagonist relative to PTH agonist.

Any suitable PTH antagonist, including the ones disclosed above, can be used in the present method. Preferably, the PTH antagonist comprises a contiguous portion of human PTH having an amino acid sequence set forth in SEQ ID NO:1 ($PTH_{1-84}$), or a nucleic acid encoding said portion of human PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues.

F. Methods for Identifying an Agent for Preventing, Treating or Delaying Osteoporosis In yet another aspect, the present invention is directed to a method for identifying an agent suitable for preventing, treating or delaying osteoporosis, which method comprises: a) measuring PTH antagonist activity in the presence and absence of a test substance; and b) identifying a substance that enhances said PTH antagonist activity as an agent suitable for preventing, treating or delaying osteoporosis.

Any suitable PTH antagonist, including the ones disclosed above, can be used in the present method. Preferably, the PTH antagonist comprises a contiguous portion of human PTH having an amino acid sequence set forth in SEQ ID NO:1 ($PTH_{1-84}$), or a nucleic acid encoding said portion of human PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues.

In comparing the activity of a PTH antagonist in the presence and absence of a test substance to assess whether the test substance is a potentiator of the PTH antagonist, it is unnecessary to assay the activity in parallel, although such parallel measurement is preferred. It is possible to measure the activity of the PTH antagonist at one time point and compare the measured activity to a historical value of the activity of the PTH antagonist. For instance, one can measure the activity of the PTH antagonist in the presence of a test substance and compare with historical value of the activity of the PTH antagonist measured previously in the absence of the test substance, and vice versa. This can be accomplished, for example, by providing the activity of the PTH antagonist on an insert or pamphlet provided with a kit for conducting the assay.

A variety of formats and detection protocols are known for performing screening assays. Any such formats and protocols may be adapted for identifying potentiator of PTH antagonist activities. The following includes a discussion of exemplary protocols.

High Throughput Screening Assays

Although the above-described assay can be conducted where a single PTH antagonist is screened against, and/or a single test substance is screened for in one assay, the assay is preferably conducted in a high throughput screening mode, i.e., a plurality of the PTH antagonists are screened against and/or a plurality of the test substances are screened for simultaneously (See generally, High Throughput Screening: The Discovery of Bioactive Substances (Devlin, Ed.) Marcel Dekker, 1997; Sittampalam et al., *Curr. Opin. Chem. Biol.*, 1(3):384-91 (1997); and Silverman et al., *Curr. Opin. Chem. Biol.*, 2(3):397-403 (1998)). For example, the assay can be conducted in a multi-well (e.g., 24-, 48-, 96-, or 384-well), chip or array format. High-throughput screening (HTS) is the process of testing a large number of diverse chemical structures against disease targets to identify "hits" (Sittampalam et al., *Curr. Opin. Chem. Biol.*, 1(3):384-91 (1997)). Current state-of-the-art HTS operations are highly automated and computerized to handle sample preparation, assay procedures and the subsequent processing of large volumes of data.

Detection technologies employed in high-throughput screens depend on the type of biochemical pathway being investigated (Sittampalam et al., *Curr. Opin. Chem. Biol.*, 1(3):384-91 (1997)). These methods include, radiochemical methods, such as the scintillation proximity assays (SPA), which can be adapted to a variety of enzyme assays (Lerner et al., *J. Biomol. Screening*, 1:135-143 (1996); Baker et al., *Anal. Biochem.*, 239:2024 (1996); Baum et al., *Anal. Biochem.*, 237:129-134 (1996); and Sullivan et al., *J. Biomol. Screening*, 2:1923 (1997)) and protein-protein interaction assays (Braunwalder et al., *J. Biomol. Screening*, 1:23-26 (1996); Sonatore et al., *Anal. Biochem.*, 240:289-297 (1996); and Chen et al., *J. Biol. Chem.*, 271:25308-25315 (1996)), and nonisotopic detection methods, including but are not limited to, colorimetric and luminescence detection methods, resonance energy transfer (RET) methods, time-resolved fluorescence (HTRF) methods, cell-based fluorescence assays, such as fluorescence resonance energy transfer (FRET) procedures (see, e.g., Gonzalez et al., *Biophys. J.*, 69:1272-1280 (1995)), fluorescence polarization or anisotropy methods ((see, e.g., Jameson et al., Methods Enzymol., 246:283-300 (1995); Jolley, *J. Biomol. Screening*, 1:33-38 (1996); Lynch et al., *Anal. Biochem.*, 247:77-82 (1997)), fluorescence correlation spectroscopy (FCS) and other such methods.

Test Substances

Test compounds, including small molecules and libraries and collections thereof can be screened in the above-described assays and assays described below to identify compounds that potentiate the activity a PTH antagonist. Rational drug design methodologies that rely on computational chemistry may be used to screen and identify candidate compounds. The compounds identified by the screening methods include any compounds and collections of compounds available, know or that can be prepared.

Compounds can be selected for their potency and selectivity of potentiation of a PTH antagonist. The assay is performed in the absence of test compound, and in the presence of increasing concentrations of the test compound. The concentration of test compound at which 50% of the PTH antagonist activity is potentiated by the test compound is the IC50 value (Potentiation Concentration) or EC50 (Effective Concentration) value for that compound. Within a series or group of test compounds, those having lower IC50 or EC50 values are considered more potent potentiators of the PTH antagonist than those compounds having higher IC50 or EC50 values. The IC50 measurement is often used for more simplistic assays, whereas the EC50 is often used for more complicated assays, such as those employing cells.

Preferred compounds according to this aspect have an IC50 value of 100 nM or less as measured in an in vitro assay for potentiation of a PTH antagonist. Especially preferred compounds have an IC50 value of less than 100 nM.

The test compounds also are evaluated for selectivity toward a PTH antagonist. As described herein, and as generally known, a test compound is assayed for its potency toward a panel of target PTH antagonists and other PTH related moieties and an IC50 value or EC50 value is determined for each test compound in each assay system. A compound that demonstrates a low IC50 value or EC50 value for the target PTH antagonist, and a higher IC50 value or EC50 value for the other PTH related moieties within the test panel, is considered to be selective toward the target PTH antagonist. Generally, a compound is deemed selective if its IC50 value or EC50 value in the target PTH antagonist assay is at least one order of magnitude less than the next smallest IC50 value or EC50 value measured in the selectivity panel of PTH antagonists.

Compounds are also evaluated for their activity in vivo. The type of assay chosen for evaluation of test compounds will depend on the pathological condition to be treated or prevented by use of the compound, as well as the route of administration to be evaluated for the test compound.

G. Methods and Kits for Preventing, Treating or Delaying Bone Metastasis

In yet another aspect, the present invention is directed to a method for preventing, treating or delaying bone metastasis in a human, which method comprises administering to a human, to which such prevention, treatment or delay is needed or desirable, an effective amount of a parathyroid hormone (PTH) antagonist or an agent that enhances production and/or antagonizing function of said PTH antagonist, wherein said PTH antagonist comprises a contiguous portion of human PTH having an amino acid sequence set forth in SEQ ID NO:1 ($PTH_{1-84}$), or a nucleic acid encoding said portion of human PTH, and said PTH antagonist has the following characteristics: a) the N-terminal amino acid residue of said PTH antagonist starts at any position spanning position 2 through position 33 of said $PTH_{1-84}$; b) the C-terminal amino acid residue of said PTH antagonist ends at any position spanning position 35 through position 84 of said $PTH_{1-84}$; and c) said PTH antagonist has a minimal length of three amino acid residues, whereby said bone metastasis is prevented, treated or delayed.

The present methods can be used to prevent, treat or delay any bone metastasis, e.g., the bone metastasis associated with or caused by breast cancer, prostate cancer or multiple myeloma. For example, the present methods can be used to prevent, treat or delay morbidity or mortality associated with the bone metastasis. In another example, the present methods can be used to prevent, treat or delay pain, pathological fractures, hypercalcemia or spinal cord compression associated with the bone metastasis.

Any suitable PTH antagonists or agents that enhances production and/or antagonizing function of the PTH antagonists, including the ones described in the present application, can be used in the present methods. The PTH antagonists or agents that enhances production and/or antagonizing function of the PTH antagonists can be administered via any suitable route. For example, the PTH antagonists or an agents that enhances production and/or antagonizing function of the PTH antagonists can be administered orally or intravenously.

The PTH antagonists or agents that enhances production and/or antagonizing function of the PTH antagonists can be used alone in the present methods. Alternatively, the PTH antagonists or agents that enhances production and/or antagonizing function of the PTH antagonists can be used in combination with a hormone therapy or a chemotherapy.

In yet another aspect, the present invention is directed to a kit, which kit comprises an above-described parathyroid hormone (PTH) antagonist or an agent that enhances production and/or antagonizing function of the PTH antagonist in a container and an instruction for using the PTH antagonist or agent in preventing, treating or delaying bone metastasis.

H. Exemplary Embodiments

Figure 1:
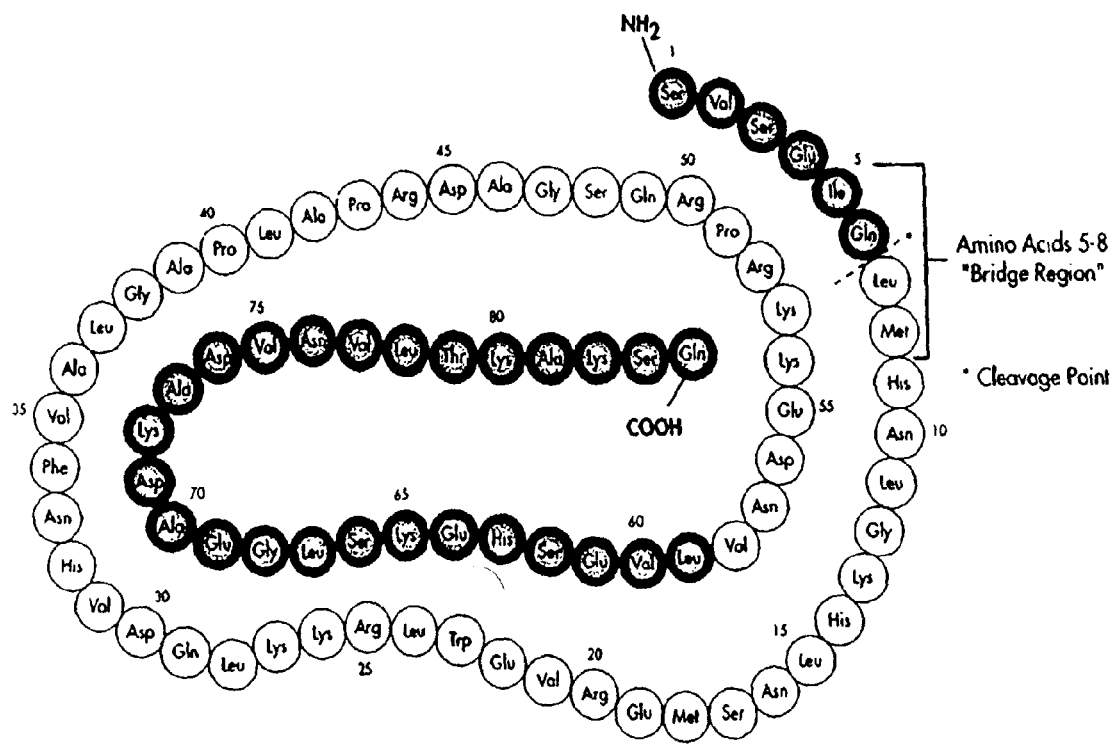
FIG. 1 is a diagrammatic view of human PTH (hPTH).

There are a number of closely analogous, species dependent forms of PTH. The amino acid sequence of hPTH or cyclase activating parathyroid hormone (CAP) is shown in FIG. 1. However, for rat PTH, bovine PTH, or porcine PTH, for example, one finds the substitutions at some of the amino acids in the hPTH sequence. For the purposes of the present embodiment, one can use interchangeably truncated forms of these PTH's, although it is preferred to use a PTH having a sequence matching the species in which the PTH antagonist is used.

Preferred PTH antagonists of the present embodiment have an amino acid sequence from between $PTH_{2-84}$ and $PTH_{34-84}$ or a conservatively substituted variant thereof exhibiting PTH antagonist activity, with the most preferred form being from between $PTH_{3-84}$ and $PTH_{28-34}$.

In order to make the present compositions, one can use any conventionally known method. For example, one can use recombinant DNA methods to produce the desired compound. Alternatively, one can use an automated peptide synthesizer, such as Model 431 made by Applied Biosystems, Inc. (Foster City, Calif., U.S.A.) Fmoc (9-fluoronylmethoxycarbonyl) can be used as the alpha-amino protecting group. All amino acids and solvents are available from Applied Biosystems and are of synthesis grade. Following synthesis, the peptide is cleaved from the resin, and side chains are de-blocked, using a cleavage cocktail containing 6.67% phenol, 4.4% (v/v) thioanisole and 8.8% ethanedithiol in trifluoroacetic acid (TFA). The cleaved peptide is precipitated and washed several times in cold diethyl ether. It is then dissolved in water and lyophilized. The crude peptide is subjected to amino acid analysis (Waters PICO-TAG System, Boston, Mass., U.S.A.) and reversed-phase HPLC using a VYDAC™ C8 column with 0.1% TFA in water and 99.9% acetonitrile in 0.1% TFA as the mobile buffers. The presence of a single major peak along with the appropriate amino acid composition is taken as evidence that the peptide is suitable for further use.

The exemplary PTH antagonist peptides exhibit both oral and parenteral activity and can be formulated in solid or liquid dosage forms for oral, parenteral, intranasal, topical, or injectable administration using known carriers, excipients, or the like. The exact amount of exemplary PTH antagonist used can vary depending upon the degree of antagonist property desired, the route of administration, or the duration of the treatment, as is known to the art.

The exemplary PTH antagonists have the ability to reduce the increase in serum calcium normally caused by PTH or a PTH agonist analog. These antagonists also possess an ability similar to a cyclase inhibiting parathyroid hormone peptide (CIP) to treat osteoporosis due to the CAP rebound effect that comes with CIP administration. The CAP rebound effect is believed to be the body's response to an administration of CIP. This response occurs when the parathyroid gland cells secrete CAP in an effort to return the CAP/CIP ratio to homeostasis with the pre-CIP administration levels. PTH antagonist administration is not accompanied by hypercalcemia and osteosarcoma, as with direct CAP administration. FIG. 5 is a graph demonstrating such a hypercalcemic prevention property. Twenty-five rats were used in a demonstration of the effect of the exemplary PTH antagonists. All of the rats had their parathyroid glands removed. Five rats received an i.v. injection of a saline control. The serum calcium of the control rats was measured and on average was lowered over time by about 0.18 mg/dl by virtue of a parathyroidectomy. Nine rats received an i.v. injection (10 μg/kg) of hPTH obtained from Bachem, AG of Bubendorf, Switzerland. The serum calcium of the hPTH rats was measured and on average was raised over time by about 0.65 mg/dl. Five rats received an equimolar i.v. injection of a $PTH_{7-84}$ (an exemplary PTH antagonist) also obtained from Bachem, AG of Bubendorf, Switzerland. The serum calcium of the PTH antagonist rats was measured and on average was lowered over time by about 0.30 mg/dl. Finally, six rats received an i.v. injection comprised of hPTH (10 μg/kg) and an equimolar amount of PTH antagonist $PTH_{7-84}$. The serum calcium of the hPTH/PTH antagonist rats was measured and on average remained substantially the same over time, raising only about 0.03 mg/dl. Thus, the exemplary composition was able to prevent the substantial serum calcium increase normally associated with an administration of hPTH to rats having hypoparathyroidism, and quite unexpectedly, is much more potent in its antagonist property than the previously reported antagonist $PTH_{3-34}$.

I. EXAMPLES

Methods

Characterization of the New "Whole" PTH IRMA Assay

This new Whole PTH two-site assay (Scantibodies Laboratories, Santee, Calif., USA) first employees and antibody that recognizes the 39-84 region of the PTH molecule. This antibody, produced in a goat and affinity purified, is present in relative excess and is immobilized onto polystyrene-coated tubes. The second antibody, also developed in a goat, was also affinity purified and recognizes only the first six amino acids (1 to 6; Ser-Val-Ser-Glu-Ile-Gln) of the human PTH molecule (FIG. 1). This anti-hPTH assay uses synthetic human PTH 1-84 as the standard, with a limit of detection of approximately 1 to 2 pg/mL. Normal values range from 5 to 35 pg/mL. The interassay and intra-assay coefficients of variation were found to be between 2 and 7% and recovery was from 96 to 106%. The Whole PTH assay was compared with the Intact PTH assay purchases from the Nichols Institute (I-Nichols, San Jan Capistrano, Calif., USA). Synthetic human PTH 1-84 and 7-84 were purchased from Bachem (Torrance, Calif. USA). To assess circulating levels of hPTH 1-84 and non-(1-84) PTH, heparinized blood samples were obtained before dialysis from 28 patients who had been maintained on chronic hemodialysis for 1.2 to 7.5 years and from 14 renal transplant patients (1 to 6 years).

Studies In Vitro

Osteoblastic cell line. To compare the biological effects of the two peptides (HPTH 1-84 and 7-84), intracellular cAMP production was measured in the rate osteosarcoma cell line ROS/17.2, which has an osteoblastic phenotype and is known to increase cAMP production in response to PTH. Cells were cultured in Ham's F12 media containing 10% fetal bovine serum. Cells were plated out in 12 well plates at a density of 30,000 cells per well and grown to confluence. Cells were washed three times with KHMS buffer at 37° C. (KCI 4.0 mmol/L, $CaCl_2$ 1.25 mmol/L, $MgSO_4$ 1.25 mmol/L, $KH_2PO_4$ 1.2 mmol/L, HEPES 10 mmol/L, NaCl 100 mmol/L, $NaHCO_3$ 37 mmol/L, and glucose 10 mmol/L, pH 7.5). cAMP production was measured using 500 μL of KHMS buffer (37°) containing isobutyl-1 methylxantine (1BMX) 1.0 mmol/L and various concentrations ($10^{-11}$ to $10^{-8}$ mol/L) of hPTH 1-84 or hPTH 7-84. After a five-minute incubation, 100 μL of 1.8 mol/L pechloric acid were added. After an additional five-minute incubation at room temperature, 100 μL of 3 mol/$KHCO_3$ were added to neutralize the acid. Samples were centrifuged at 3000 rpm for 15 minutes, and the supernatants were assayed for cAMP [26].

Analysis of PTH in human parathyroid glands. Human parathyroid glands were placed in ice-cold phosphate-buffered saline and processed within 30 minutes of parathyroidectomy. Aliquots of parathyroid tissue were dissected, weighed, and homogenized in 500 μL of a buffer containing 100 mmol/L Tris-HCl, pH 7.5, 100 mmol/L NaCl, 1 mol/L DL-dithiothreitol, and a complete TM protease inhibitor cocktail (Boehringer-Mannheim, Mannheim, Germany). Homogenates were sonicated three times for 30 seconds each at 0° C. and centrifuged at 10,000×g for 15 minutes. Supernatants were kept at −70° C. until measurements of 1-84 PTH, non(1-84) PTH, and total protein were performed.

Studies In Vivo

Calcemic response. Normal female Sprague-Dawley rats weighing 225 to 250 g (Harlan, Indianapolis, Ind., USA) were parathyroidectomized (PTX) and fed a 0.02% calcium diet. Rats with a plasma calcium below 7.0 mg/dL after overnight fasting were included in the study. A 20 μg dose of hPTH 1-84 or 7-84 was given intraperitoneally to PTX rats in four doses of 5 μg each at 30-minute intervals (0, 30, 60, and 90 minutes). For control studies, the rats received vehicle (saline solution) alone. Blood was drawn via the tail at 0, 60, 90, and 120 minutes. For competition experiments, rats received an injection of hPTH 7-84 10 minutes prior to each injection of hPTH 1-84. The molar ratio of hPTH 7-84:hPTH 1-84 was 1:1.

Phosphaturic response. Normal female Sprague-Dawley rats weighing 225 to 250 g were prepared for clearance studies under light anesthesia. Polyethylene catheters (PE50) were placed in the femoeral artery for the collection of blood and measurement of blood pressure (Blood Pressure Analyzer; Micro-Medic, Inc., Louisville, Ky., USA), in the femoral vein for infusion and in the bladder for the collection of urine. Rats were placed in Plexiglass holders and allowed to recover from the effect of the anesthetic for one hour. A priming dose (0.6 mL) of chemical inulin in saline was administered over a period of three minutes to achieve a plasma inulin level between 50 and 100 mg/mL. A solution of saline containing inulin to maintain this level and calcium gluconate to deliver 0.5 mg. calcium was infused at the rate of 0.03 mL/min. After equilibration, a total of four 30-minute urine collections was obtained.

To assess the effect of hPTH 1-84 on phosphate excretion, urine was collected during two control periods, after which rats received a priming bolus of 1.8 μg of HPTH 1-84 followed by a sustained infusion that delivered a total of 8.2 μg of I-PTH. After an equilibration period of 20 minutes, two 30-minute urine collections were obtained. In competition experiments, HPTH 7-84 was given five minutes prior to hPTH 1-84 at a molar ratio of 4:1.

Blood samples and blood pressure measurements were recorded at the beginning and end of the baseline period, at the beginning of the PTH infusion period, and at the end of the study. The concentration of inulin in plasma and urine was determined by the method of Führ, Kaczmarczyk, and Kruttgen, *Klin Wochenschr*, 33:729-730 (1955). The estimation of the glomerular filtration rate (GFR) by inulin clearance and the calculation of the fractional urinary excretion rate of phosphorus ($FE_{PO4}$) were performed in the standard fashion. Blood samples were centrifuged, and plasma phosphorus and calcium concentrations were measured.

Serum Chemistries

Total plasma calcium levels were determined using an atomic absorption spectrophotometer (model 110B; Perkin Elmer, Norwalk, Conn., USA). Plasma phosphorus levels were determined using an autoanalyzer (COBAS MIRA Plus; Roche, Newark, N.J., USA).

Statistical Analysis

Results are expressed as mean±SEM. N indicates the number of samples. The paired t-test was employed to examine statistical significance, unless otherwise indicated in the text.

Results

Specificity of IRMA Assays for hPTH 1-84

Figure 2:
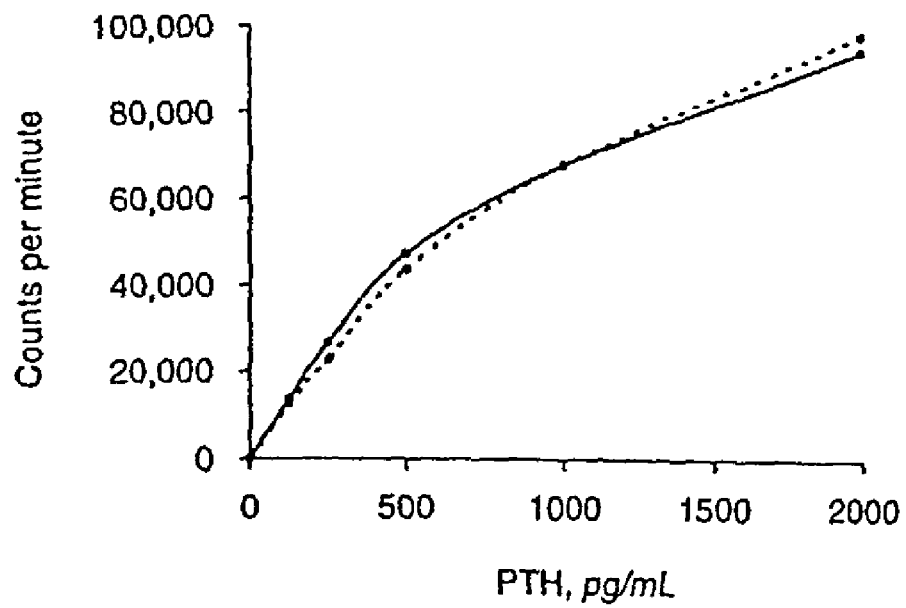
FIG. 2 illustrates comparison of the recognition of hPTH 1-84 and HPTH 7-84 by the Nichols I-PTH assay. The Nichols 1-PTH assay does not differentiate between hPTH 1-84 (solid line) and hPTH 7-84 (dashed line).

Initial studies compared the ability of the Nichols Intact (I-Nichols) PTH assay and the new Whole PTH assay to discriminate between the HPTH 1-84 and hPTH 7-84 molecules. FIG. 2 shows that the Nichols "intact" PTH assay did not discriminate between human PTH 1-84 and 7-84. However, as depicted in FIG. 3, studies performed using the Whole PTH assay show that hPTH 1-84 was detected with a high degree of sensitivity, whereas hPTH 7-84 was undetectable, even at a concentration as high as 10,000 pg/mL.

Studies In Vitro

The results of cAMP production by ROS/17.2 cells exposed to hPTH 1-84 or hPTH 7-84 are shown in FIG. 4. Unlike hPTH 7-84, hPTH 1-84 increased cAMP production in a does-dependent manner. hPTH 1-84 ($10^{-8}$ mol/L) increased intracellular cAMP from 18.1±1.25 to 738±4.13 nmol/well. On the other hand, the same concentration of hPTH 7-84 had no effect on cAMP (N=6).

Studies In Vivo in Rats

We next examined the hPTH 7-84 fragment as a potential competitive inhibitor of hPTH 1-84 in bone by measuring changes in serum calcium in PTX rats. FIG. 5 shows that the administration of hPTH 1-84 to PTX rats fed a 0.02% calcium diet increased plasma calcium by 0.65±0.10 mg/dL (N=9, P.<0.001, ANOVA). With the administration of vehicle alone, plasma calcium changed slightly in accordance with PTX (−0.17±0.10 mg/dL, N=5). A slight but significant decrease was observed in the rats receiving hPTH 7-84 (0.30±0.08 mg/dL, N=5, P<0.05). When both peptides were given together in a 1:1 molar ratio, the calcemic response induced by the administration of hPTH 1-84 alone decreased by 94% (N=6, P<0.001, ANOVA. Thus in this model, hPTH 7-84 significantly inhibits hPTH 1-84 induction of bone calcium mobilization.

The phosphaturic effects of these two peptides were then evaluated (FIG. 6). The GFR did not change in rats infused with hPTH 1-84 (1.8±0.3 vs. 1.8±0.1 mL/min), whereas fractional excretion of phosphate ($FE_{PO4}$) increased from 11.9±2.4 to 27.7±2.4% (N=10, P<0.001). When hPTH 7-84 was given simultaneously with hPTH 1-84, the GFR increased from 2.1±0.1 to 2.6±0.2 mL/min (N=8, P<0.05). However, despite this increase in GFR, the increase in $FE_{PO4}$ induced by treatment with hPTH 1-84 was significantly decreased by 50.2% (P<0.01). by virtue of the coadministration of hPTH 7-84.

Studies in Humans

FIG. 7 shows that the values for plasma PTH were higher in all 28 patients on chronic dialysis when measured with the I-Nichols assay compared with the Whole assay. The median PTH values were 523 versus 344 pg/ml (P<0.001), respectively. A regression analysis of these data is shown in FIG. 8.

The association between plasma levels of non-(1-84) PTH, "likely" hPTH 7-84, and plasma calcium and phosphorus was next examined in 20 patients maintained on chronic dialysis (FIG. 9). There was a positive correlation between the percentage of non-(1-84) PTH and serum calcium (P<0.002), but no correlation with plasma phosphorus (data not shown). These studies were performed only in those patients in whom there were values for calcium, phosphorous, and PTH from the same blood sample [20].

In a group of 14 renal transplant patients the percentage of non-(1-84) PTH was found to be 44.1±3.1% of the total PTH, as measured by the I-Nichols assay and the Whole PTH assay (FIG. 10). The absolute PTH value with the I-Nichols assay was 132.9±39.9 compared with 79.8±24.8 pg/mL (P<0.005) with the Whole PTH assay.

Finally, we examined whether intracellular cleavage of the hPTH 1-84 molecule occurs in the parathyroid gland, thus producing the non (1-84) PTH fragment. Surgically excised parathyroid glands from six uremic patients maintained on chronic dialysis were studied. FIG. 11 shows that non (1-84) PTH fragments exist in the cell lysates from these parathyroid glands and represent 41.8±3.2% (P<0.05) of the total intracellular PTH measured by the "intact" PTH assay (that is, 1-84 PTH and most likely 7-84 PTH).

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

The invention claimed is:

1. A method for treating or delaying a disease or disorder associated with excessive bone mineral loss in a mammal, wherein the mammal is presently undergoing PTH agonist therapy,
which method comprises administering to a mammal, to which such treatment or delay is needed or desirable, an effective amount of a parathyroid hormone (PTH) antagonist,
wherein the PTH antagonist is a protein or a peptide, selected from the group consisting of $PTH_{2-84}$, $PTH_{3-84}$, $PTH_{4-84}$, $PTH_{5-84}$, $PTH_{6-84}$, $PTH_{7-84}$, $PTH_{8-84}$, $PTH_{9-84}$, $PTH_{10-84}$, $PTH_{11-84}$, $PTH_{12-84}$, $PTH_{13-84}$, $PTH_{14-84}$, $PTH_{15-84}$, $PTH_{16-84}$, $PTH_{17-84}$, $PTH_{18-84}$, $PTH_{19-84}$, $PTH_{20-84}$, $PTH_{21-84}$, $PTH_{22-84}$, $PTH_{23-84}$, $PTH_{24-84}$, $PTH_{25-84}$, $PTH_{26-84}$, $PTH_{27-84}$, $PTH_{28-84}$, $PTH_{29-84}$, $PTH_{30-84}$, $PTH_{31-84}$, $PTH_{32-84}$, and $PTH_{33-84}$,
whereby said disease or disorder associated with excessive bone mineral loss is treated or delayed.

2. The method of claim 1, which is used to treat or delay bone density decrease caused by or associated with said PTH agonist therapy.

3. The method of claim 1, wherein the PTH agonist has the PTH adenylate cyclase activating activity.

4. The method of claim 1, wherein the mammal has an abnormal PTH agonist and/or PTH antagonist level.

5. A method for treating or delaying a disease or disorder associated with excessive bone mineral loss in a mammal that is presently undergoing PTH agonist therapy, which method comprises administering to the mammal to which such treatment or delay is needed or desirable, an effective amount of a parathyroid hormone (PTH) antagonist, wherein said PTH antagonist comprises a contiguous portion of pig PTH having an amino acid sequence set forth in SEQ ID NO:2, dog PTH having an amino acid sequence set forth in SEQ ID NO:3, bovine PTH having an amino acid sequence set forth in SEQ ID NO:4, rat PTH having an amino acid sequence set forth in SEQ ID NO:5 or chicken PTH having an amino acid sequence set forth in SEQ ID NO:6,
wherein the PTH antagonist is a protein or a peptide, selected from the group consisting of $PTH_{2-84}$, $PTH_{3-84}$, $PTH_{4-84}$, $PTH_{5-84}$, $PTH_{6-84}$, $PTH_{7-84}$, $PTH_{8-84}$, $PTH_{9-84}$, $PTH_{10-84}$, $PTH_{11-84}$, $PTH_{12-84}$, $PTH_{13-84}$, $PTH_{14-84}$, $PTH_{15-84}$, $PTH_{16-84}$, $PTH_{17-84}$, $PTH_{18-84}$, $PTH_{19-84}$, $PTH_{20-84}$, $PTH_{21-84}$, $PTH_{22-84}$, $PTH_{23-84}$, $PTH_{24-84}$, $PTH_{25-84}$, $PTH_{26-84}$, $PTH_{27-84}$, $PTH_{28-84}$, $PTH_{29-84}$, $PTH_{30-84}$, $PTH_{31-84}$, $PTH_{32-84}$, and $PTH_{33-84}$,
whereby said disease or disorder associated with excessive bone mineral loss is treated or delayed.

6. The method of claim 1, wherein the mammal is a human.

7. The method of claim 6, wherein the human has an abnormal PTH antagonist level or an abnormal comparative value between PTH agonist and PTH antagonist.

8. The method of claim 6, wherein the human has an abnormal PTH agonist level.

9. The method of claim 7, wherein the human has an abnormal comparative value between PTH agonist and PTH antagonist, and the abnormal comparative value between PTH agonist and PTH antagonist is determined by determining and comparing at least two of the parameters selected from the group consisting of the level of the PTH agonist, the PTH antagonist and the sum of the PTH agonist and the PTH antagonist level.

10. The method of claim 9, wherein the comparison is in the form of a ratio, a proportion or subtraction difference.

11. The method of claim 9, wherein the human has a PTH agonist/PTH antagonist ratio more than 2 and the method is used to bring the PTH agonist/PTH antagonist ratio within a range from about 1 to about 2.

12. The method of claim 6, wherein the PTH antagonist is $PTH_{7-84}$.

13. The method of claim 6, wherein the PTH antagonist is administered in a solid or a liquid dosage form.

14. The method of claim 6, wherein the PTH antagonist is administered orally, parenterally, intranasally, topically, injectably or via a liposome.

15. The method of claim 6, wherein the PTH antagonist is administered as a bolus.

16. The method of claim 6, wherein the PTH antagonist is administered continuously.

17. The method of claim 6, wherein the PTH antagonist is administered intermittently or is multiply administered.

18. The method of claim 6, wherein the PTH antagonist is administered over a course of about 1, 2, 2-6, 6-12, or 12-24 hours.

19. The method of claim 6, wherein the PTH antagonist is administered over a course of about 1, 2, 2-5, 5-14, or 14-60 days.

20. The method of claim 6, wherein the PTH antagonist is administered over a course of about 1, 2, 2-6, 6-12, 12-24, 24-48, or more months.

21. The method of claim 6, wherein the PTH antagonist is administered intraperitoneally daily for about 2 months and then the administration is stopped for about 1 month and then resumed intraperitoneally daily for about 2 months.

22. The method of claim 6, wherein the PTH agonist is a contiguous portion of human $PTH_{1-84}$ having the following characteristics:
    a) the N-terminal amino acid residue of said PTH agonist starts at position 1 of $PTH_{1-84}$, and
    b) the C-terminal amino acid residue of said PTH agonist ends at any position spanning position 34 through position 84 of said $PTH_{1-84}$.

23. The method of claim 6, wherein the PTH agonist is $PTH_{1-84}$, and the PTH antagonist is $PTH_{7-84}$.

24. The method of claim 1, which is used to treat bone density decrease caused by or associated with said PTH agonist therapy.

25. The method of claim 1, which is used to delay bone density decrease caused by or associated with said PTH agonist therapy.

26. The method of claim 24, wherein the PTH agonist is $PTH_{1-84}$, and the PTH antagonist is $PTH_{7-84}$.

27. The method of claim 25, wherein the PTH agonist is $PTH_{1-84}$, and the PTH antagonist is $PTH_{7-84}$.

* * * * *

SEQUENCE LISTING

<160> NUMBER OF SEQ ID NOS: 6

<210> SEQ ID NO 1
<211> LENGTH: 84
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asn Lys Ala Asp Val Asn Val Leu Thr Lys
65                  70                  75                  80

Ala Lys Ser Gln

<210> SEQ ID NO 2
<211> LENGTH: 84
<212> TYPE: PRT
<213> ORGANISM: Pig

<400> SEQUENCE: 2

Ser Val Ser Glu Ile Gln Leu Met His Asn Leu Gly Lys His Leu Ser
1               5                   10                  15

Ser Leu Glu Arg Val Glu Trp Leu Arg Lys Lys Leu Gln Asp Val His
            20                  25                  30

Asn Phe Val Ala Leu Gly Ala Ser Ile Val His Arg Asp Gly Gly Ser
        35                  40                  45

Gln Arg Pro Arg Lys Lys Glu Asp Asn Val Leu Val Glu Ser His Gln
    50                  55                  60

Lys Ser Leu Gly Glu Ala Asp Lys Ala Ala Val Asp Val Leu Ile Lys
65                  70                  75                  80

Ala Lys Pro Gln

<210> SEQ ID NO 3
<211> LENGTH: 84
<212> TYPE: PRT
<213> ORGANISM: Dog

<400> SEQUENCE: 3

Ser Val Ser Glu Ile Gln Phe Met His Asn Leu Gly Lys His Leu Ser
1               5                   10                  15

```
Ser Met Glu Arg Val Glu Trp Leu Arg Lys Lys Leu Gln Asp Val His
            20                  25                  30

Asn Phe Val Ala Leu Gly Ala Pro Ile Ala His Arg Asp Gly Ser Ser
            35                  40                  45

Gln Arg Pro Leu Lys Lys Glu Asp Asn Val Leu Val Glu Ser Tyr Gln
        50                  55                  60

Lys Ser Leu Gly Glu Ala Asp Lys Ala Asp Val Asp Val Leu Thr Lys
65                  70                  75                  80

Ala Lys Ser Gln

<210> SEQ ID NO 4
<211> LENGTH: 84
<212> TYPE: PRT
<213> ORGANISM: Bovine

<400> SEQUENCE: 4

Ala Val Ser Glu Ile Gln Phe Met His Asn Leu Gly Lys His Leu Ser
 1               5                  10                  15

Ser Met Glu Arg Val Glu Trp Leu Arg Lys Lys Leu Gln Asp Val His
            20                  25                  30

Asn Phe Val Ala Leu Gly Ala Ser Ile Ala Tyr Arg Asp Gly Ser Ser
            35                  40                  45

Gln Arg Pro Arg Lys Lys Glu Asp Asn Val Leu Val Glu Ser His Gln
        50                  55                  60

Lys Ser Leu Gly Glu Ala Asp Lys Ala Asp Val Asp Val Leu Ile Lys
65                  70                  75                  80

Ala Lys Pro Gln

<210> SEQ ID NO 5
<211> LENGTH: 84
<212> TYPE: PRT
<213> ORGANISM: Rat

<400> SEQUENCE: 5

Ala Val Ser Glu Ile Gln Leu Met His Asn Leu Gly Lys His Leu Ala
 1               5                  10                  15

Ser Val Glu Arg Met Gln Trp Leu Arg Lys Lys Leu Gln Asp Val His
            20                  25                  30

Asn Phe Val Ser Leu Gly Val Gln Met Ala Ala Arg Glu Gly Ser Tyr
            35                  40                  45

Gln Arg Pro Thr Lys Lys Glu Glu Asn Val Leu Val Asp Gly Asn Ser
        50                  55                  60

Lys Ser Leu Gly Glu Gly Asp Lys Ala Asp Val Asp Val Leu Val Lys
65                  70                  75                  80

Ala Lys Ser Gln

<210> SEQ ID NO 6
<211> LENGTH: 88
<212> TYPE: PRT
<213> ORGANISM: Chicken

<400> SEQUENCE: 6

Ser Val Ser Glu Met Gln Leu Met His Asn Leu Gly Glu His Arg His
 1               5                  10                  15

Thr Val Glu Arg Gln Asp Trp Leu Gln Met Lys Leu Gln Asp Val His
            20                  25                  30
```

-continued

```
Ser Ala Leu Glu Asp Ala Arg Thr Gln Arg Pro Arg Asn Lys Glu Asp
        35                  40                  45

Ile Val Leu Gly Glu Ile Arg Asn Arg Arg Leu Leu Pro Glu His Leu
        50                  55                  60

Arg Ala Ala Val Gln Lys Lys Ser Ile Asp Leu Asp Lys Ala Tyr Met
65                  70                  75                  80

Asn Val Leu Phe Lys Thr Lys Pro
                    85
```